(12) United States Patent
Mendelsohn et al.

(10) Patent No.: US 7,026,280 B2
(45) Date of Patent: *Apr. 11, 2006

(54) LV V-HAEMORPHIN-7 NEUROACTIVE PEPTIDE AND METHODS OF USE

(75) Inventors: Frederick A. O. Mendelsohn, Eltham (AU); Siew Yeen Chai, Burwood East (AU); Ingrid Moeller, Northcote (AU); Peter G. Aldred, Bunin Yong (AU); Ian A. Smith, Hampton (AU); Rebecca A. Lew, Port Melbourne (AU)

(73) Assignee: Howard Florey Institute of Experimental Physiology, Victoria (AU)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/147,490

(22) PCT Filed: Jul. 9, 1997

(86) PCT No.: PCT/AU97/00436

§ 371 (c)(1),
(2), (4) Date: May 13, 1999

(87) PCT Pub. No.: WO98/01465

PCT Pub. Date: Jan. 15, 1998

(65) Prior Publication Data

US 2002/0147129 A1    Oct. 10, 2002

(30) Foreign Application Priority Data

Jul. 9, 1996   (AU) .................................... PO0893

(51) Int. Cl.
*A61K 38/00*   (2006.01)
*C07K 5/00*   (2006.01)
*C07K 14/00*   (2006.01)

(52) U.S. Cl. .................... 514/2; 530/300; 530/350
(58) Field of Classification Search ................ 530/300, 530/350; 514/2–21
See application file for complete search history.

(56) References Cited

U.S. PATENT DOCUMENTS 5,063,206 A * 11/1991 Bridge et al.
5,599,907 A * 2/1997 Anderson et al.
5,861,483 A * 1/1999 Wolpe et al.

OTHER PUBLICATIONS

Kandel et al., Principles in Neural Science, Elsevier, 1991, pp. 1056-1057.*
Wilkinson et al., Neurosurgery, Apr. 1994, 34(4):665-68.*
Relton et al., J. of Exp. Med., Aug. 1991, 174(2):305-10.*
Furey, et al, 1997, Proc. Natl. Acad. Sci., 94: 6512-6516.*
Peng, et al, 1997, Jpn. J. Pharmacol., 74: 261-266.*
Neurobiology of Disease, 1990, Pearlman and Collins, eds, Oxford, pp. 306-308.*
Gallagher & Rapp, 1997, Annual Review of Psychology, vol. 48, pp. 339-370.*
Molchan, et al, 1992, Brain Res. Rev., 17: 215-226.*
Blokland, et al, 1995, Brain Res Rev., 21(3):285-300.*
Davies P, & Maloney A, 1976, Lancet, Letters to the Editor, p. 1403.*
Naveen & Kohli, 2003, Indian Journal of Pharmacology, 35: 104-108.*
Ye, et al, 1999, Journal of Pharmacol. Exp Ther; 288(2): 814-819.*
Ebert & Kirch, 1998, European Journal of Clinical Investigation, vol. 28 Issue 11, p. 944.*
Lee, et al, 2003, J. Pharmacol. Exp. Therap, 305: 205-211.*
I. Moeller et al, "The Globin Fragement LVV-Hemorphin-7 is an Endogenous Ligand for the $AT_4$ Receptor in the Brian", Journal of Neurochemistry vol. 68, No. 6, Jun. 1997, pp 2530-2537.

(Continued)

Primary Examiner—Janet L. Andres
Assistant Examiner—Sandra Wegert
(74) Attorney, Agent, or Firm—Foley & Lardner LLP

(57) ABSTRACT

The invention relates to neuroactive peptides or analogues thereof, having at least one of the biological activities of angiotensin IV, and which comprise the sequence Leu-Val-Val-Tyr-Pro-Trp-Thr-Gln-Arg-Phe, to methods of modulating neuronal activity, and to pharmaceutical composition thereof.

9 Claims, 15 Drawing Sheets

OTHER PUBLICATIONS

I. Garreau et al, "VV-hemorphin-7 and LVV-hemorphin-7 Released during in vitro Peptic hemoglobin Hydrolysis are Morphinomimetic Peptides", Neuropeptides, vol. 28, 1995, pp. 243-250.

J. Piot, et al, "Isolation and Characterization of Two Opiod Peptides from a Bovine Hemoglobin Peptic Hydrolysate", Biochemical and Biophysical Research Communications, vol. 189, No. 1, Nov. 1992, pp. 101-110.

E. Giamsta et al, "Isolation of a Hemoglobin-Derived Opiod Peptide from Cerebrospinal Fluid of Patients with Cerebrovascular Bleedings", Biochemical and Biophysical Research Communications, vol. 184, No. 2, Apr. 30, 1992, pp. 1060-1066.

R. Chang et al, "Isolation and Structure of Several Peptides from Porcine Hypothalami", Biochimica et Biophysica Acta, 1980, vol. 625, pp. 266-273.

J. Szikra et al, "Receptor Binding Properties of a Hemorphin Analogue in Rat Brain Membrane Preparations", Neurobiology, vol. 4, 1996, pp. 279-280.

A. Karelin, et al, "Isolation of Endogenous Hemorphin-Related Hemoglobin Fragments from Bovine Brain", vol. 22, No. 1, Jul. 15, 1994, pp. 410-415.

C. Woo et al, "cDNA Sequences of Two β-Globin Genes in Sprague-Dawley Rat", Nucleic Acids Research, vol. 17, No. 21, 1989, pp. 8870.

* cited by examiner

OLIGONUCLEOTIDE SEQUENCES:

H170: 5' CTGGTTGTCTACCCCTGGACTCAGAG 3'
H171: 5' CTCTGAGTCCAGGGGTAGACAACCAG 3'
H172: 5' CTCAGGATCCACATGCAGCTTATCACAG 3'
H173: 5' CAGCACAACCACTAGCACATTGCC 3'

```
                                    10        20        30
EX                         CACAAACTCAGAAACAGACACCATGGTGCACCTGA
RNBGLO   TGCTTCTGACATAGTTGTGTTGACTCACAAACTCAGAAACAGACACCATGGTGCACCTGA
            10        20        30        40        50        60
         40        50        60        70        80        90
EX       CTGATGCTGAGAAGGCTGCTGTTAATGGCCTGTGGGGAAAGGTGAACCCTGATGATGTTG
RNBGLO   CTGATGCTGAGAAGGCTGCTGTTAATGGCCTGTGGGGAAAGGTGAACCCTGATGATGTTG
            70        80        90       100       110       120
        100       110       120       130       140       150
EX       GTGGCGAGGCCCTGGGCAGGCTGCTGGTTGTCTACCCTTGGACCCAGAGGTACTTTGATA
RNBGLO   GTGGCGAGGCCCTGGGCAGGCTGCTGGTTGTCTACCCTTGGACCCAGAGGTACTTTGATA
           130       140       150       160       170       180
        160       170       180       190       200       210
EX       GCTTTGGGGACCTGTCCTCTGCCTCTGCTATCATGGGTAACCCTAAGGTGAAGGCCCATG
RNBGLO   GCTTTGGGGACCTGTCCTCTGCCTCTGCTATCATGGGTAACCCTAAGGTGAAGGCCCATG
           190       200       210       220       230       240
        220       230       240       250       260       270
EX       GCAAGAAGGTGATAAACGCCTTCAATGATGGCCTGAAACACTTGGACAACCTCAAGGGCA
RNBGLO   GCAAGAAGGTGATAAACGCCTTCAATGATGGCCTGAAACACTTGGACAACCTCAAGGGCA
           250       260       270       280       290       300
        280       290       300       310       320       330
EX       CCTTTGCTCATCTGAGTGAACTCCACTGTGACAAGCTGCATGTGGATCCTGAGAACTTCA
RNBGLO   CCTTTGCTCATCTGAGTGAACTCCACTGTGACAAGCTGCATGTGGATCCTGAGAACTTCA
           310       320       330       340       350       360
        340       350       360       370       380       390
EX       GGCTCCTGGGCAATATGATTGTGATTGTGTTGGGCCACCACCTGGGCAAGGAATTCACCC
RNBGLO   GGCTCCTGGGCAATATGATTGTGATTGTGTTGGGCCACCACCTGGGCAAGGAATTCACCC
           370       380       390       400       410       420
        400       410       420       430       440       450
EX       CCTGTGCACAGGCTGCCTTCCAGAAGGTGGTGGCTGGAGTGGCCAGTGCCCTGGCTCACA
RNBGLO   CCTGTGCACAGGCTGCCTTCCAGAAGGTGGTGGCTGGAGTGGCCAGTGCCCTGGCTCACA
           430       440       450       460       470       480
        460       470       480       490       500       510
EX       AGTACCACTAAACCTCTTTTCCTGCTCTTGTCTTTGTGCAATGGTCAATTGTTCCCAAGA
RNBGLO   AGTACCACTAAACCTCTTTTCCTGCTCTTGTCTTTGTGCAATGGTCAATTGTTCCCAAGA
           490       500       510       520       530       540
        520       530       540       550       560       570
EX       GAGCATCTGTCAGTTGTTGTCAAAATGACAAAGACCTTTGAAAATCTGTCCTACTAATAA
RNBGLO   GAGCATCTGTCAGTTGTTGTCAAAATGACAAAGACCTTTGAAAATCTGTCCTACTAATAA
           580       590       600       610
EX       AAGGCATTTACTTTCACTGCAAAAAAAAAAAAAAAAAA
RNBGLO   AAGGCATTTACTTTCACTGC
```

FIG. 12

```
                                        10        20        30
EX                           CACAAACTCAGAAACAGACACCATGGTGCACCTGA
                                                    M  V  H  L 40        50        60        70        80        90
EX CTGATGCTGAGAAGGCTGCTGTTAATGGCCTGTGGGGAAAGGTGAACCCTGATGATGTTG
    T  D  A  E  K  A  A  V  N  G  L  W  G  K  V  N  P  D  D  V 100       110       120       130       140       150
EX GTGGCGAGGCCCTGGGCAGGCTGCTGGTTGTCTACCCTTGGACCCAGAGGTACTTTGATA
    G  G  E  A  L  G  R  L  L  V  V  Y  P  W  T  Q  R  Y  F  D
       160       170       180       190       200       210
EX GCTTTGGGGACCTGTCCTCTGCCTCTGCTATCATGGGTAACCCTAAGGTGAAGGCCCATG
    S  F  G  D  L  S  S  A  S  A  I  M  G  N  P  K  V  K  A  H
        220       230       240       250       260       270
EX GCAAGAAGGTGATAAACGCCTTCAATGATGGCCTGAAACACTTGGACAACCTCAAGGGCA
    G  K  K  V  I  N  A  F  N  D  G  L  K  H  L  D  N  L  K  G
        280       290       300       310       320       330
EX CCTTTGCTCATCTGAGTGAACTCCACTGTGACAAGCTGCATGTGGATCCTGAGAACTTCA
    T  F  A  H  L  S  E  L  H  C  D  K  L  H  V  D  P  E  N  F
        340       350       360       370       380       390
EX GGCTCCTGGGCAATATGATTGTGATTGTGTTGGGCCACCACCTGGGCAAGGAATTCACCC
    R  L  L  G  N  M  I  V  I  V  L  G  H  H  L  G  K  E  F  T
        400       410       420       430       440       450
EX CCTGTGCACAGGCTGCCTTCCAGAAGGTGGTGGCTGGAGTGGCCAGTGCCCTGGCTCACA
    P  C  A  Q  A  A  F  Q  K  V  V  A  G  V  A  S  A  L  A  H
        460       470       480       490       500       510
EX AGTACCACTAAACCTCTTTTCCTGCTCTTGTCTTTGTGCAATGGTCAATTGTTCCCAAGA
    K  Y  H  *
        520       530       540       550       560       570
EX GAGCATCTGTCAGTTGTTGTCAAAATGACAAAGACCTTTGAAAATCTGTCCTACTAATAA 580       590       600       610
EX AAGGCATTTACTTTCACTGCAAAAAAAAAAAAAAAAAAA
```

FIG. 13

LVV-HAEMORPHIN-7 NEUROACTIVE PEPTIDE AND METHODS OF USE

This invention relates to neuroactive peptides, and in particular to peptides which have the ability to act as analogues of angiotensin IV. The peptides of the invention bind with high affinity and specificity to a variety of sites in the central nervous system, and are useful as modulators of motor and cognitive function, and of neuronal development.

BACKGROUND OF THE INVENTION

The renin-angiotensin system has diverse roles in the regulation of body fluid and electrolyte balance and blood pressure control. These actions are exerted in a variety of target organs, including the cardiovascular system, adrenal glands, kidney and central and peripheral nervous systems, by both the circulating hormone and hormone locally produced in tissues. Most of these actions are exerted by the octapeptide, angiotensin II, although the C-terminal heptapeptide angiotensin III has some activity. The hexapeptide NH2-Val Tyr Ile His Pro Phe-COOH (SEQ ID No:10), corresponding to the 3-8 fragment of angiotensin II (ie. amino acids 3-8), is also called angiotensin IV (Ang IV), and has until recently been believed to be an inactive degradation product devoid of biological activity.

However, Harding and co-workers have confirmed an earlier report (Braszko et al, 1988) that Ang IV has central nervous system activity, and can modify learning and behaviour (Wright et al, 1995). In addition, Ang IV has vasoactive effects, and can dilate cerebral arteries (Haberl et al, 1991) and increase renal blood flow (Swanson et al, 1992). This, coupled with the discovery of highly specific, high affinity sites for Ang IV binding in bovine adrenal and other tissues, has reawakened interest in the hexapeptide, and the subject has been comprehensively reviewed (Wright et al 1995).

Ang IV has been associated with the central nervous system effects of increasing stereotypy behaviour (Braszko et al, 1988) and facilitating memory retrieval in passive avoidance studies (Braszko et al, 1988; Wright et al, 1995). Ang IV also dilates cerebral arterioles (Haberl et al, 1991), and increases renal blood flow (Swanson et al, 1992).

Receptor autoradiographic studies have revealed a widely abundant but selective and characteristic distribution of binding sites for $[^{125}I]$Ang IV (known as the $AT_4$ receptor) in the guinea pig, sheep and monkey central nervous systems, in regions associated with cholinergic neurons and in somatic motor and sensory associated areas (Miller-Wing et al, 1993; Moeller et al, 1995, Moeller et al, 1996). In addition, Ang IV binding sites are abundant in supraspinal components of the autonomic nervous system, and in the spinal cord are found in sympathetic preganglionic neurons, in the dorsal root ganglia, and in Lamina II of the dorsal horn, and in the motor neurons of the ventral horn (Moeller et al, 1995).

The distribution of the Ang IV binding site differs from the localization of the Ang II $AT_1$ or $AT_2$ receptors. In addition, the pharmacology of each receptor is distinct in that the Ang IV site exhibits a low to very low affinity for [Sar$^1$Ile$^8$]Ang II, the non-subtype selective Ang II antagonist, and losartan (du Pont-Merck) and PD 123319 (Parke-Davis), the specific $AT_1$ and $AT_2$ receptor antagonists respectively (Miller-Wing et al, 1993; Swanson et al, 1992; Hanesworth et al, 1993). Conversely, Ang II receptors show a low affinity for the Ang IV binding site (Bennett and Snyder, 1976).

The wide distribution of the Ang IV binding site in motor, sensory and cholinergic regions suggests important roles for this peptide in the central nervous system. However, a physiological action of the peptide in neurons has yet to be clearly defined.

Numerous neurotransmitters and neuropeptides have been associated with the regulation of neuronal development. Acetylcholine inhibits neurite outgrowth from embryonic chicken ciliary ganglion cells and sympathetic neurons (Pugh and Berg, 1994; Small et al, 1995), and rat hippocampal neurons (Muttson, 1988). Conversely, vasoactive intestinal peptide stimulates superior cervical ganglion branching (Pincus et al, 1990) and somatostatin increases neuronal sprouting from Helisoma buccal ganglion neurons (Bulloch, 1987).

We have now surprisingly found that the peptide LVV-haemorphin-7, derived from β-globin, acts as an agonist at the $AT_4$ receptor, and is the endogenous ligand for the $AT_4$ receptors in the brain. We have characterised its pharmacological activity. This enables us to design novel agonists and antagonists of Ang IV action.

SUMMARY OF THE INVENTION

According to a first aspect, the invention provides a method of modulating motor neuron activity, cholinergic neuron activity, or neuronal development, comprising the step of administering an effective amount of a neuroactive peptide having at least one of the biological activities of angiotensin IV as herein defined, comprising the amino acid sequence: Leu-Val-Val-Tyr-Pro-Trp-Thr-Gln-Arg-Phe, (SEQ ID NO:1) or a biologically-active analogue or fragment of said peptide to a mammal in need of such treatment. This aspect of the invention specifically includes the use of decapeptide sequence referred to above in the method of the invention which relies on a previously unknown and unsuspected activity of the decapeptide.

It will be clearly understood that the sequence of the invention may be modified by conservative amino acid substitutions, insertions, deletions or extensions, provided that the biological activity is retained. Such variants may, for example, include sequences comprising D-amino acids, non-naturally occurring amino acids, and/or amino acid analogues. Thus the analogue may be a peptidomimetic compound.

Preferably the mammal is a human.

The Ang IV agonist and antagonist compounds according to the invention are useful in the treatment of a variety of conditions, including but not limited to:

Dementia, including Alzheimer's disease

Other neurodegenerative disorders involving cholinergic pathways, motor pathways, or sensory pathways, such as motor neurone disease sensory and motor peripheral neuropathies brain or spinal cord injury due to trauma, hypoxia or vascular disease.

In a second aspect, the invention provides a non-peptide analogue of the peptide of the invention. This non-peptide analogue is to be understood to encompass modifications or substitutions of the peptide structure which are designed to improve the bioavailability, metabolic stability, half-life in the body, or to modify the biological activity, of the compound of the invention. Such non-peptide analogues are known in the art, for example compounds in which the peptide backbone is replaced by a non-peptide chain, and are often referred to as peptidomimetic compounds. Alternatively, in one or more of the peptide linkages the order of the nitrogen and carbon atoms can be reversed to form a pseudo peptide bond. One or more of the amino acid side-chains may be replaced by an analogous structure of greater stability. Many other such variations will occur to the person skilled in the art. The only requirement is that the overall 3-dimensional structure is sufficiently preserved that ability to bind to the $AT_4$ receptor at suitable affinity is retained. Using modern methods of peptide synthesis and combinatorial chemistry, it is possible to synthesize and test very large numbers of analogues within a short space of time, and such synthesis and screening is routinely carried out by pharmaceutical companies.

Considerable information is available regarding the structural features of Ang IV peptides which are necessary for high affinity, and these results may be used as guidelines for modification of the peptides of the invention. See for example Wright et al, 1995.

The person skilled in the art will appreciate that by modifying the sequence or by constructing a non-peptide analogue the activity of the compound of the invention can be very considerably modified. Not only can improvement in activity be obtained, it is also possible to obtain compounds which bind to the $AT_4$ receptor in such a way that Ang IV activity is inhibited. Such inhibitory compounds can have the ability to antagonize the activity of Ang IV. The person skilled in the art will readily be able to synthesize modified peptides and peptide analogues and to test whether they have activity as Ang IV agonists or antagonists, using methods well known in the art.

According to a third aspect, the invention provides a method of screening for putative agonists or antagonists of the effect of LVV-haemorphin-7 on neuronal activity, comprising the step of testing the ability of the compound to stimulate or inhibit the effect of LVV-haemorphin-7 on a biological activity selected from the group consisting of modifying learning, modifying behaviour, vasoactive effects, dilation of cerebral arteries, increase in renal blood flow, increase in stereotypy behaviour, facilitating memory retrieval, neurite modelling and alleviation of the effects of spinal cord injury.

Thus according to a fourth aspect, the invention also provides compounds which are able to act as agonists or antagonists of the neuroactive peptides of the invention.

DETAILED DESCRIPTION OF THE INVENTION

The invention will be now described in detail by way of reference only to the following non-limiting examples, and to the figures, in which FIG. 1 shows competition curves derived from prefrontal cortical sections incubated with [$^{125}$I]Ang IV in the presence of increasing concentrations of the following unlabelled ligands: ▲ Ang IV, □ Ang II, ■ Ang III, Δ Ang II(1–7), ● losartan and ○ PD 123319. Values are the mean of four sections, each from two animals. B/Box100 expressed as a percentage available receptors occupied;

FIG. 2 shows the results of competition binding studies showing the inhibition of [$^{125}$I]Ang IV binding to E13 chicken chorioallantoic membranes with varying concentrations of unlabelled compounds: ▲ Ang IV, ◊Nle$^1$-AIV, Δ CGP 42112, □ Ang II, ▼ Nle$^1$-Y-I-amide, ✱WSU-4042, ■ [Sar$^1$Ile$^8$]Ang II, ● PD 123319 and ○ losartan. Values are expressed as a percentage of total binding, and are pooled from two experiments. B/Box100=% of available receptors occupied;

FIG. 3 summarizes competition binding studies showing the inhibition of $^{125}$I[Sar$^1$Ile$^8$]Ang II binding to E13 chicken chorioallantoic membranes with varying concentrations of unlabelled compounds: ■ [Sar$^1$Ile$^8$]Ang II, □ Ang II, Δ CGP 42112, ◊Nle$^1$-AIV, ▲ Ang IV, ○ losartan, ● PD 123319, ✱WSU-4042 and ▼ Nle$^1$-Y-I-amide. Values are expressed as a percentage of total bnding, and are pooled from two experiments. B/Box100=% of available receptors occupied;

FIG. 4 shows the effect of Ang IV on neurite outgrowth from E11 chicken sympathetic neurons. Values are expressed as a percentage of control levels, and are depicted as the mean±standard error of the mean (SEM). The results are pooled from 3 experiments, each with at least 40 neurite measurements. * indicates a significant difference from control values using Bonferroni's test;

FIG. 5 shows the effect of 10 nM Ang IV on neurite outgrowth in the presence of 1 µM Nle$^1$-Y-I-amide, WSU-4042, Nle$^1$-AIV, [Sar$^1$Ile$^8$]Ang II, losartan, PD 123319 and CGP 42112. Values are expressed as a percentage of control levels, and are depicted as the mean±S. E. M. The results are pooled from 3 experiments, each with at least 40 neurite measurements. * indicates a significant difference from control values using Bonferroni's test;

FIG. 6 shows the effect of 10 nM Ang II on neurite outgrowth in the presence of 1 µM Nle$^1$-Y-I-amide, WSU-4042, Nle$^1$-AIV, [Sar$^1$Ile$^8$]Ang II, losartan, PD 123319 and CGP 42112. Values are expressed as a percentage of control levels, and are depicted as the mean±S. E. M. The results are pooled from 3 experiments, each with at least 40 neurite measurements. * indicates a significant difference from control values using Bonferroni's test;

FIG. 7 illustrates the binding of $^{125}$I-angiotensin IV to sheep spinal cord. The arrow indicates the site of damage to the spinal cord;

FIG. 8 summarizes the results of competition binding studies showing the inhibition of [$^{125}$I]LVV-haemorphin-7 binding to sheep cerebellar cortical membranes with varying concentrations of unlabelled compounds: Δ Ang IV, Δ LVV-haemorphin-7, □ Ang III, □ Ang II, ○ PD 123319, ○ losartan, * naloxone and ∇ haloperidol. Values are the mean of three experiments. B/Box100=% of available receptors occupied;

FIG. 9 summarizes the results of competition binding studies showing the inhibition of [$^{125}$I]Ang IV binding to sheep cerebellar cortical membranes with varying concentrations of unlabelled compounds: Δ Ang IV, Δ LVV-haemorphin-7, □ AngIII, □ AngII, ○ PD 123319, ○ losartan, * naloxone and ∇ haloperidol. Values are the mean of three experiments. B/Box100=% of available receptors occupied;

FIG. 10 is a schematic diagram illustrating the position of the oligonucleotide probes used for cloning and PCR experiments. (A) schematic diagram of the β-globin precursor (SEQ ID NO:1) showing relevant position and direction of oligonucleotides used. The shaded region represents the LVV-haemorphin-7 sequence, which is given below. (B) sequences of the oligonucleotides H170 to H173 (SEQ ID Nos:2 to 5 respectively) used in this study;

FIG. 12 shows the complete nucleotide sequence of Clone EX (SEQ ID NO:6) and RNBGLO (SEQ ID NO:9) and FIG. 13 shows the nucleotide sequence (SEQ ID NO:7) and derived amino acid sequence (SEQ ID NO:8) of the rat EX clone. The region of the potential LVV-haemorphin-7 is shown in bold.

Figure 14:
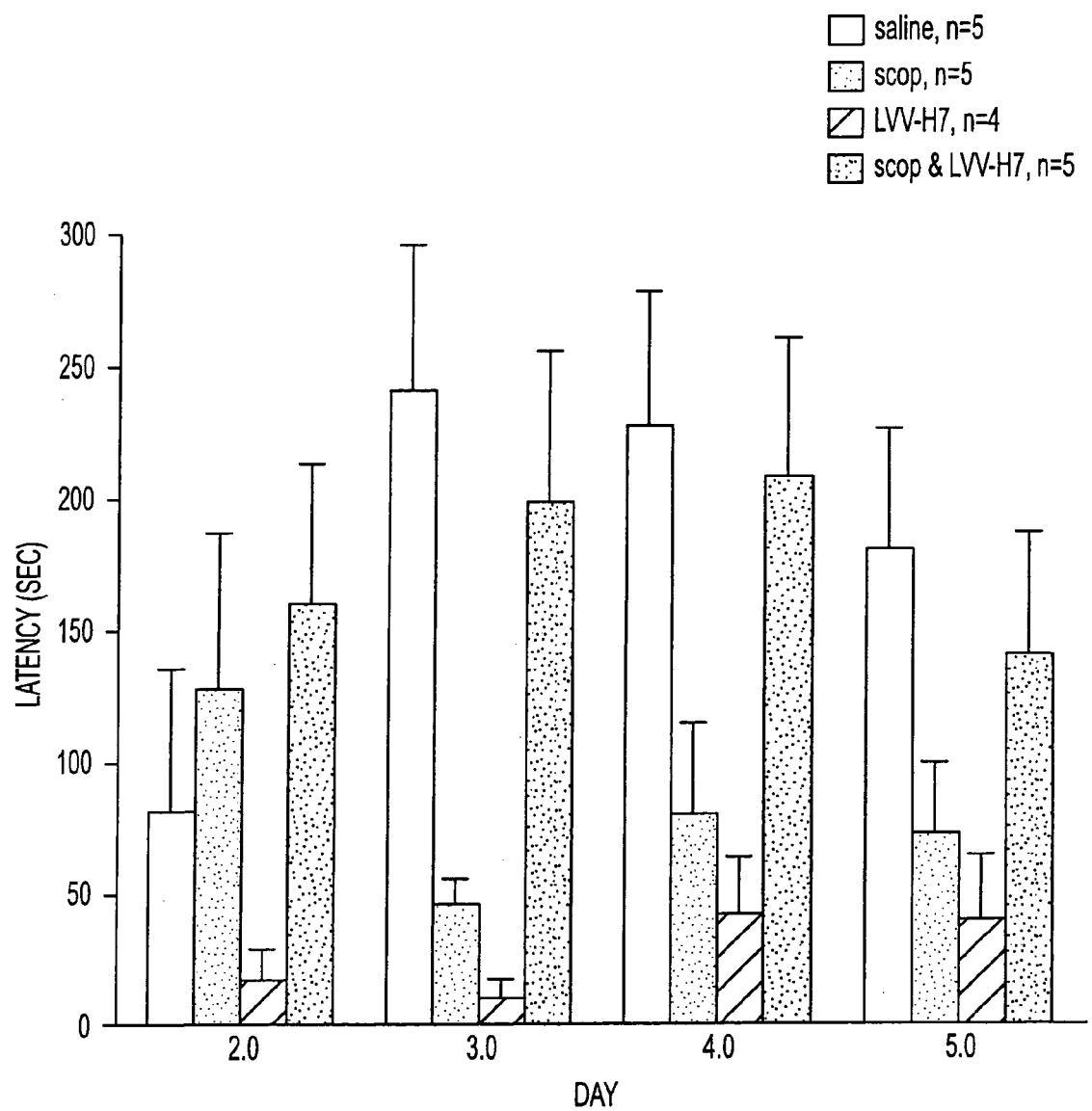

FIG. 14 summarizes the effects of LVV-haemorphin-7 on the performance of scopolamine-treated rats in a passive avoidance task.

Figure 15:
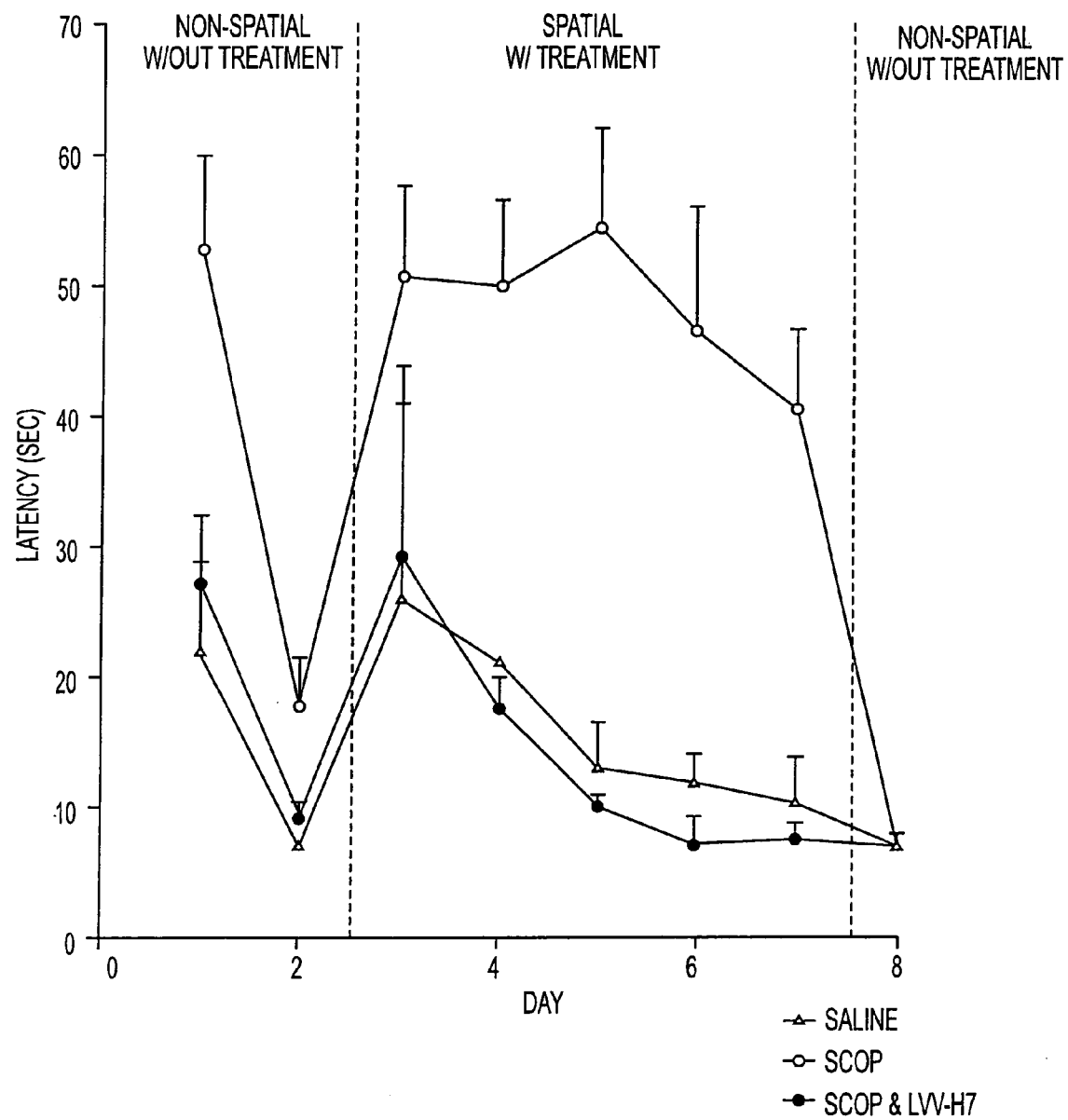

FIG. 15 summarizes the effects of LVV-haemorphin-7 on the performance of scopolamine-treated rats in a water maze acquisition trial.

The unlabelled ligands, Ang IV (Peninsula Laboratories, Calif. USA), Ang II and the Ang II antagonist [Sar$^1$Ile$^8$]Ang II (Sigma, Mo. USA), the Ang II partial agonist CGP 42112 (Ciba-Geigy, Basle Switzerland), the Ang II ATI antagonist, losartan (Du Pont Merck Pharmaceutical Company, Del. USA), the Ang II AT$_2$ antagonist, PD 123319 (Parke-Davis, Mich. USA-Ms. C. L. Germain), and the Ang IV analogues, WSU 4042, Nle$^1$-Y-I-amide and Nle$^1$-AIV (prepared as previously described by Sardinia et al, 1993), were used at final concentrations ranging from $10^{-9}$ to $10^{-4}$ M.

EXAMPLE 1

Mapping of Angiotensin AT$_4$ Receptors in Monkey Brain

Figure 1:
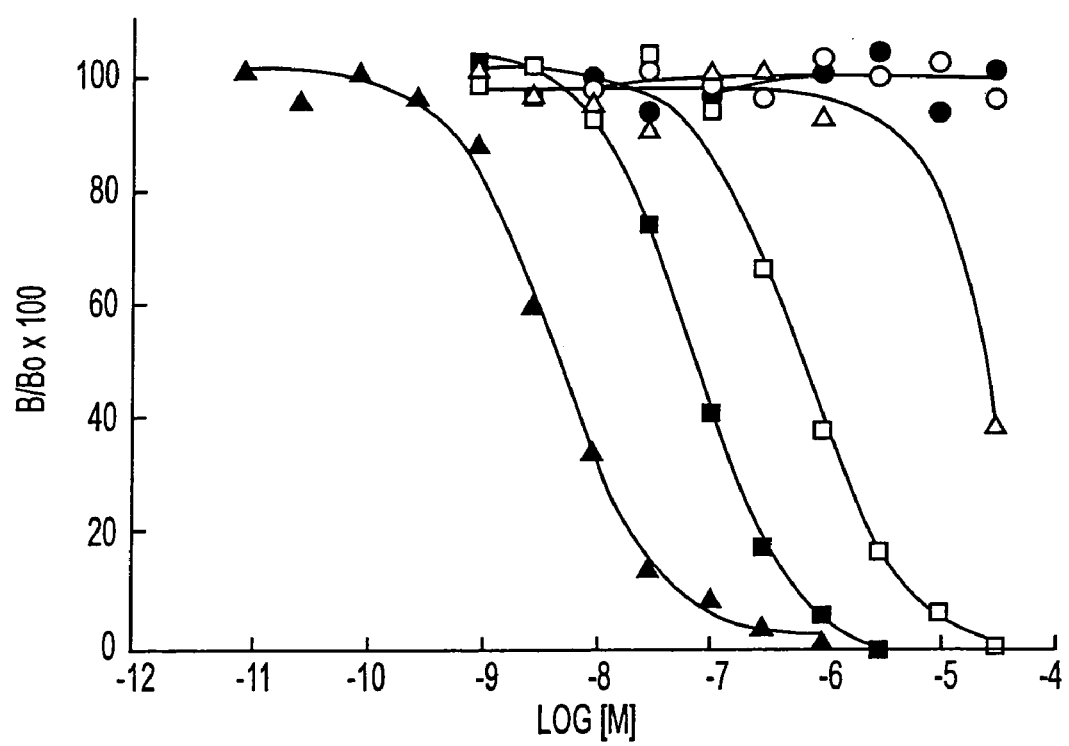

We mapped the distribution of the receptors for Ang IV (AT$_4$ receptors) in the *Macaca fascicularis* brain using in vitro receptor autoradiography in order to determine if the widespread and distinct distribution of the receptors that are found in the guinea pig brain is also found in primates. The binding sites were initially characterized pharmacologically in competition studies on prefrontal cortical brain sections. These results are summarized in FIG. 1. Ang IV, Ang III and Ang II competed for [$^{125}$I]Ang IV binding with IC$_{50}$s of 5 nM, 80 nM and 730 nM respectively, while Ang II(1–7) was a weak competitor (IC$_{50}$ of 24 mM). The AT$_1$ receptor antagonist, losartan (du Pont-Merck) and the AT$_2$ receptor antagonist, PD 123319 (Parke-Davis), were inactive, even at concentrations of 10 mM. These pharmacological properties are similar to those previously described for the AT$_4$ receptor in bovine adrenal and guinea pig septal membranes, confirming that we were mapping the distribution of the same receptor.

The distribution of the AT$_4$ receptor was remarkable, in that its distribution extended throughout several neural systems. This is summarized in Table 1. The most striking finding was the localization of this receptor in motor nuclei and motor-associated regions. These included the ventral horn spinal motor neurons, all cranial nerve motor nuclei including the oculomotor, trochlear, facial and hypoglossal nuclei, and the dorsal motor nucleus of the vagus. Receptors were also present in the vestibular, reticular and inferior olivary nuclei, the granular layer of the cerebellum, and the Betz cells of the motor cortex. Moderate AT$_4$ receptor density was seen in all cerebellar nuclei, ventral thalamic nuclei and the substantia nigra pars compacta, with a lower receptor density being observed in the caudate nucleus and putamen. The localization of the AT$_4$ receptor in all levels of the motor hierarchy in the central nervous system implies an important role for the binding site in motor activity.

TABLE 1

Localization and Quantitation of the AT$_4$ Receptor in the *Macaca fascicularis* Brain

| Region | AT$_4$ receptor density dpm/mm2 (mean ± SD) |
|---|---|
| Caudate nucleus | 48 ± 2 |
| Vertical limb of the diagonal band* | 86 ± 3 |
| Basal nucleus of Meynert* | 81 ± 5 |
| Granular layer of the dentate gyrus | 117 ± 11 |
| CA1 | 45 ± 4 |
| CA3 | 41 ± 3 |
| Supraoptic retrochiasmatic nucleus* | 93 ± 7 |
| Ventral posterior lateral/medial nuclei | 35 ± 2 |
| Red nucleus* | 44 ± 2 |
| Oculomotor nucleus* | 44 ± 1 |
| Pontine nuclei | 50 ± 2 |
| Lateral geniculate | 52 ± 2 |
| Mo5* | 84 ± 3 |
| Facial nucleus* | 90 ± 4 |
| Hypoglossal nucleus* | 93 ± 8 |
| Inferior olive | 76 ± 10 |
| Granular layer of the cerebellum | 126 ± 10 |
| Molecular layer of the cerebellum | 47 ± 6 |

Values are the mean of four sections from one animal and are representative of the relative densities of AT$_4$ receptors.
*Values are determined from the overall area and not from individual cell bodies which exhibit higher binding.

In addition to the somatic motor nuclei and autonomic preganglionic motor nuclei, abundant AT$_4$ receptors were also found in other cholinergic systems and their projections, including the nucleus basalis of Meynert, vertical limb of the diagonal band and the hippocampus. Apart from being a neurotransmitter in motor neurons, acetylcholine is also implicated in cognition, since anti-cholinergic drugs induce memory disorders and confusion; in Alzheimers's disease, neuronal loss occurs in the cholinergic-rich basal nucleus of Meynert. Ang IV has been shown by two independent studies to facilitate memory retrieval in passive and conditioned avoidance tests (Braszko et al, 1988; Wright et al, 1993), and, when administered intracerebroventricularly, induces c-fos expression in the hippocampus (Roberts et al, 1995). Together with the presence of high densities of AT$_4$ receptors in this region, these observations suggest that Ang IV may play an important role in the modulation of cognitive function.

AT$_4$ receptors were also observed in sensory regions, with moderate levels in spinal trigeminal, gracile, cuneate and thalamic ventral posterior nuclei, and in the somatosensory cortex. While receptor density was low in sensory neurons when compared with that observed in motor and cognitive areas, the AT$_4$ receptor was located throughout most sensory-associated areas, including the lamina II of the spinal cord, gracile, cuneate and spinal trigeminal nuclei, ventral posterior thalamic and lateral geniculate nuclei and the sensory cortex, suggesting a substantial involvement with sensory activity. This distribution pattern has also been observed in the guinea pig and sheep brain. As shown in Example 2, abundant AT$_4$ receptors were also observed in sheep dorsal root ganglia.

EXAMPLE 2

Mapping of Angiotensin $AT_4$ Receptors in Sheep Spinal Cord

We extended the localization of the $AT_4$ receptors to the sheep spinal cord, to investigate if the strong presence of the $AT_4$ receptors in supraspinal motor and sensory regions persists in the spinal cord.

When the binding characteristics of [$^{125}$I]Ang IV were assessed in the eighth cervical segment (C8) of the sheep spinal cord, we found that the affinities of the different unlabelled ligand in competing for the binding were similar to those observed for the monkey brain.

In the sheep spinal cord, high densities of $AT_4$ receptors were found in lamina IX in the ventral horns of all segments examined. At a cellular level, the binding was found overlying the cytoplasm of lateral and medial motor neurons and in their processes, but binding was absent from the cell nuclei. Whilst a clearly defined function of the Ang IV binding site is yet to be determined, the association with motor activity is strengthened in view of its abundant localization in the motor neurones in the ventral horn of the spinal cord, in addition to its strong presence in supraspinal motor areas.

High densities of $AT_4$ receptors were also found in the lateral tip of lamina VII of all thoracic segments and lumbar segments L1 to L4, which corresponded with sympathetic preganglionic neurons in the intermediolateral cell column. However, binding was absent from L5 and L6 and from the sacral segments S1 and S2.

In the dorsal root ganglia associated with all spinal segments, high densities of $AT_4$ receptors were found in the cytoplasm of small and large cell bodies of the sensory neurons, but not in the satellite cells, nor in the endoganglionic connective tissue. In laminae I and II, the terminal fields of the dorsal root ganglia sensory afferents, only a low abundance of the receptor was noted in lamina II. Despite the low levels of $AT_4$ receptors in lamina II, their high abundance in the dorsal root ganglia and their consistent but low levels in most supraspinal sensory areas suggest that $AT_4$ receptors may still play a role in the processing of sensory information.

Low levels of the $AT_4$ receptors were also found in the blood vessels which extended radially to the pial surface, in the blood vessels of the anterior and posterior fissures, and in the ependyma of the central canal. Ang IV has been reported to induce an endothelium-dependent dilation of rabbit pial arterioles, and in rats Ang IV reverses acute cerebral blood flow reduction after experimental subarachnoid haemorrhage.

Our localization studies suggest that $AT_4$ receptors are quite distinct from the known angiotensin receptors—the $AT_{1a}$, $AT_{1b}$ and $AT_2$ receptors—in terms of their pharmacological specificity and their pattern of distribution in the brain and spinal cord. Furthermore, the pattern of distribution of the $AT_4$ receptors suggests that they may be involved in the function of neurones involved in motor function, sensory function and cholinergic systems, including cognition.

EXAMPLE 3

Characterization of Embryonic Chicken Ang IV and Ang II Binding Sites

In order to characterize the pharmacology of the embryonic chicken $AT_4$ and Ang II receptors, chorioallantoic membranes (CAM) from embryonic day 13 (E13) chickens were used. The membranes were removed and frozen in isopentane cooled to $-40°$ C.

a) Characterization of the Embryonic Chicken Ang IV Binding Site

CAM were homogenized in 30 ml of a hypotonic buffer (50 mM Tris, pH 7.4, 5 mM EDTA) and then centrifuged for 10 min at 500 g and 4° C. The supernatant fraction was removed and centrifuged for 20 min at 40,000 g and 4° C. The resulting pellet was rehomogenized in 2 ml of hypotonic buffer, and the final volume of the homogenate was adjusted to give a protein concentration of 10 mg/ml, as determined by the Biorad protein assay. The binding assay contained CAM (100 µg of protein), 0.14 µCi of [$^{125}$]Ang IV (approximately 260 pM), and competing ligand, in a total volume of 270 µl in a 50 mM Tris buffer, pH 7.4, containing 150 mM NaCl, 5 mM EDTA, 100 µM phenylmethylsulfonyl fluoride, 20 µM bestatin and 0.1% (w/v) bovine serum albumin. The binding system was incubated at 37° C. for 2 h.

b) Characterization of the Embryonic Chicken Ang II Binding Site

CAM were prepared as described above with the following exceptions. The isotonic buffer contained 50 mM Tris, pH 7.4 and 6.5 mM $MgCl_2$ and the hypotonic buffer contained 50 mM Tris, pH 7.4, 6.5 mM $MgCl_2$, 125 mM NaCl and 0.2% (w/v) bovine serum albumin. In addition, the peptidase inhibitors, leupeptin, lisinopril, phosphoramidon, Plummer's inhibitor and bestatin, each used at a 1 µM concentration and 1 mM benzamidine and 2.5 mM phenanthroline, were included in both buffers.

Figure 2:
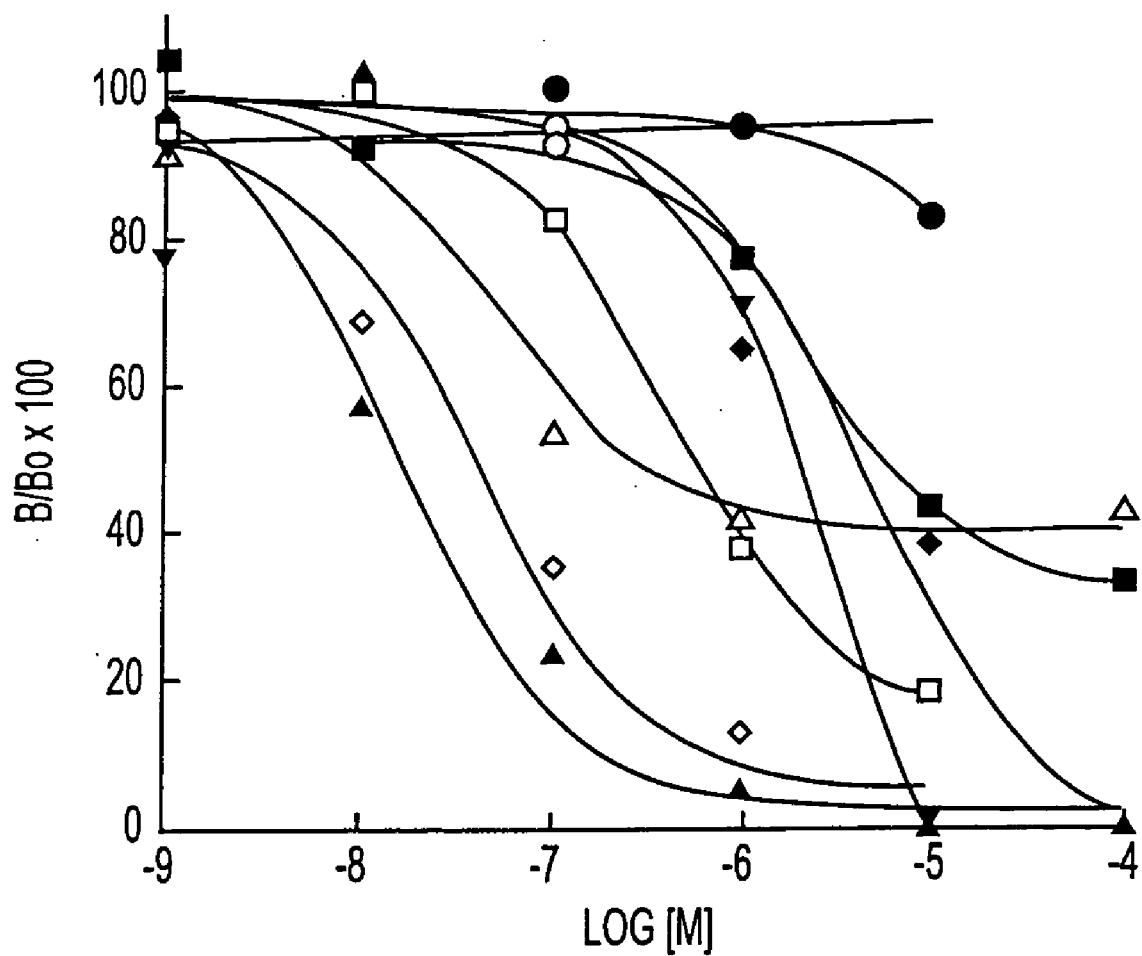

In binding competition studies on E13 chicken CAM, [$^{125}$I]Ang IV binding was strongly inhibited by Ang IV and $Nle^1$-AIV ($IC_{50}$s of 18 and 43 nM respectively), whereas WSU-4042, $Nle^1$-Y-I-amide and Ang II were weaker competitors with $IC_{50}$s of 5, 2.2 and 0.65 µM respectively, and losartan and PD 123319, were inactive at concentrations up to 10 µM. [$Sar^1Ile^8$]Ang II and CGP 42112 were effective at only competing for 50% of the sites, and then only at concentrations of 10 and 0.5 µM respectively. These results are summarized in FIG. 2.

Figure 3:
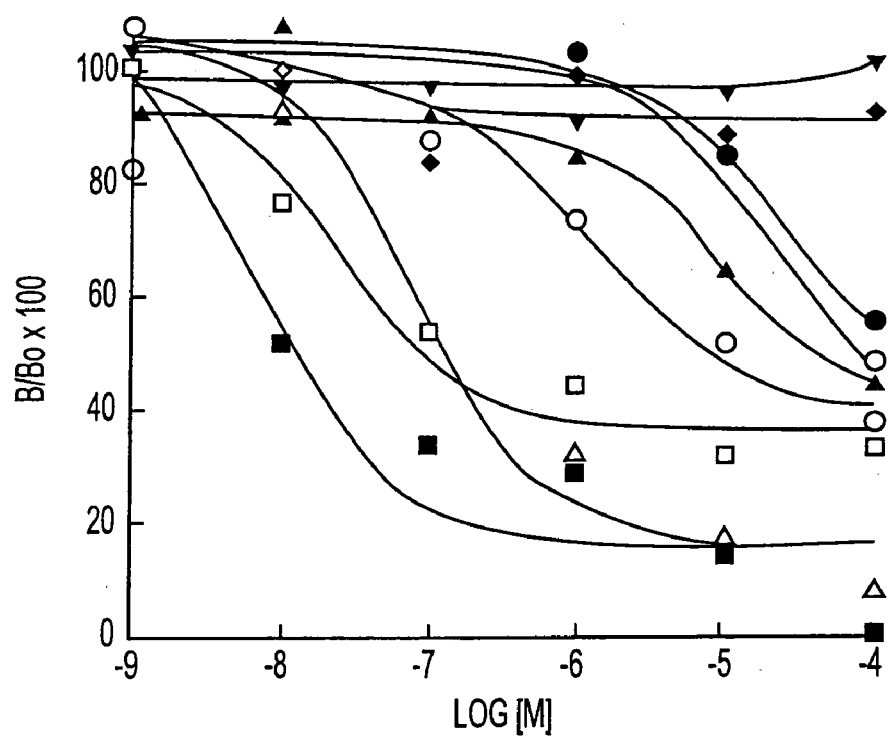

In studies of $^{125}$I[$Sar^1Ile^8$]Ang II binding to CAM, Ang II, [$Sar^1Ile^8$]Ang II and CGP 42112 competed for binding with $IC_{50}$s of 100, 13 and 180 nM respectively, whilst Ang IV, $Nle^1$-AIV and losartan were very weak competitors ($IC_{50}$s of 50, 8 and 100 µM respectively). PD 123319, WSU-4042 and $Nle^1$-Y-I-amide exhibited $IC_{50}$s greater than 100 µm. These results are shown in FIG. 3.

EXAMPLE 4

Effects of Ang IV on Neurite Outgrowth

The wide distribution of the $AT_4$ receptors in motor, sensory and cholinergic regions suggests important roles for this peptide in the central nervous system. However, a physiological action of Ang IV in neurons has yet to be clearly defined. Numerous neurotransmitters and neuropeptides have been associated with the regulation of neuronal development. For instance, acetylcholine inhibits neurite outgrowth from embryonic chicken ciliary ganglion cells, sympathetic neurons, and rat hippocampal neurons. Conversely, vasoactive intestinal peptide stimulates superior cervical ganglion branching and somatostatin increases neuronal sprouting from Helisoma buccal ganglion neurons.

We determined whether Ang IV has a trophic role in the central nervous system by examining its effects on neurite outgrowth from cultured embryonic chicken sympathetic neurons.

Sympathetic ganglia from E11 chickens were dissociated using trypsin/Versene, and were cultured in 24 well plates in DMEM and Ham's F12 medium which contained 1% (v/v) insulin-transferrin-selenium-X growth supplement (Gibco BRL, Maryland USA), 100 mM putrescine, 1.67 mg/ml prostaglandin F2α, 6.67 ng/ml progesterone, and 5 ng/ml nerve growth factor (Sigma, Mo. USA). Neurons were allowed to adhere to the wells (approximately 2 h) before being given a 24 h treatment of peptides and/or their antagonists. Peptides and antagonists used were added to the cultures 0.5 h prior to either Ang IV or Ang II addition. Ang IV dose response curves were performed over the concentration range $10^{-11}$ to $10^{-5}$ M. Culture dishes were coated with 0.1 mg/ml polylysine and then given three washes with phosphate-buffered saline (PBS) before being coated with 10 μg/ml laminin. Wells were washed with PBS before being used for culture.

At the conclusion of the experiment, the culture medium was removed from the wells, the neurons were fixed with 2.5% glutaraldehyde in PBS for 20 min and examined under a phase-contrast microscope, attached to an MD30 Plus image analysis software (Adelaide, Australia). The length of neurites (longer than 50 μm) of every neuron examined was measured. A minimum of forty neurite measurements was taken per treatment group, and each experimental treatment was performed at least in triplicate.

At the conclusion of the experiment, the viability of the cells were confirmed by exclusion of 0.1% aniline blue.

Figure 4:
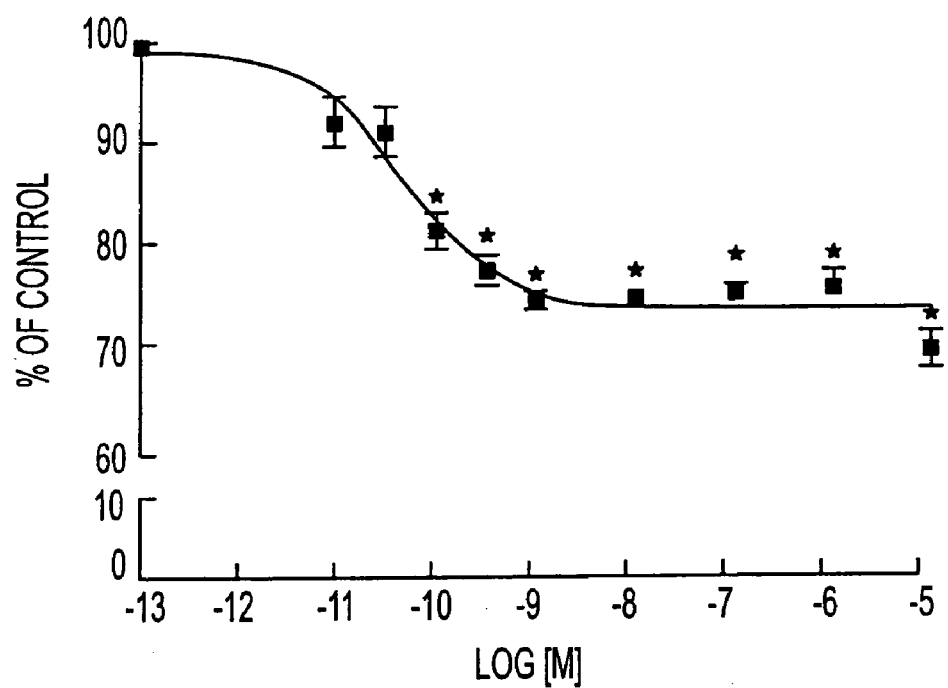
Figure 5:
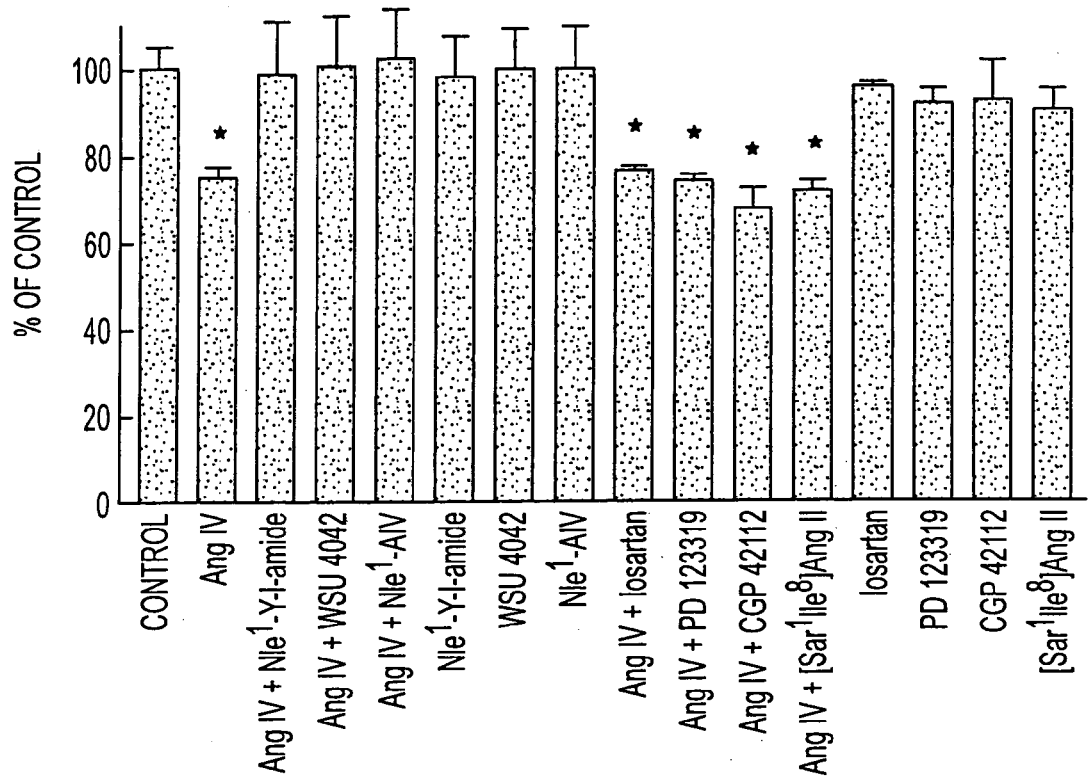

In cultures of embryonic (E11) chicken sympathetic neurons, Ang IV inhibited neurite outgrowth in a dose-dependent manner, with a threshold at $10^{-11}$ M, half maximal inhibition at $10^{-10}$ M and a maximal effect at $10^{-9}$ M. Between $10^{-9}$ to $10^{-5}$ M, outgrowth was maximally inhibited ($P<0.05$). These results are shown in FIG. 4. At $10^{-8}$ M Ang IV, the inhibition of neurite outgrowth was totally reversed by 1 μM of the Ang IV analogues WSU-4042, Nle$^1$-Y-I-amide, and Nle$^1$-AIV. The effects of the analogues alone were not statistically different from control values. In contrast to the Ang IV analogues, the Ang II antagonist, [Sar$^1$Ile$^8$]Ang II, the AT$_1$ and AT$_2$ antagonists, losartan and PD 123319, and the Ang II partial agonist, CGP 42112, had no effect on the Ang IV response, as shown in FIG. 5.

Figure 6:
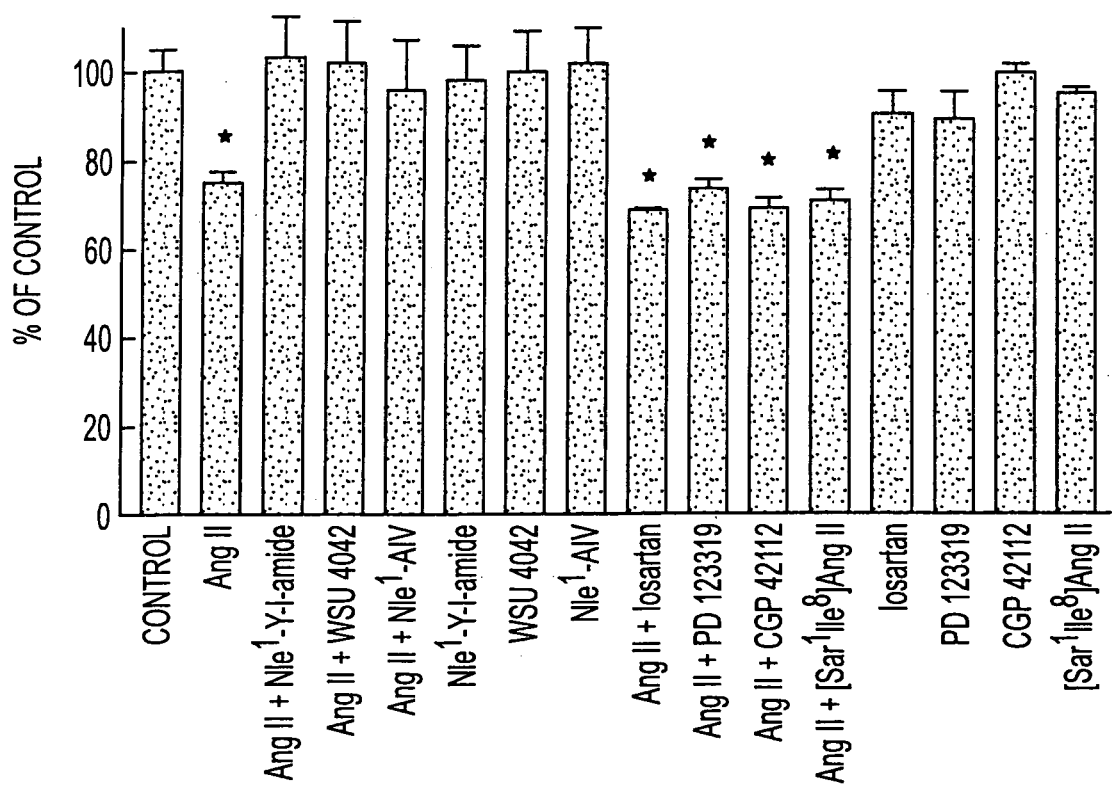

At $10^{-8}$ M Ang II, neurite outgrowth was inhibited by 25%, which was highly significant. The Ang IV analogues completely reversed this effect, whilst the Ang II antagonists [Sar$^1$Ile$^8$]Ang II, losartan, PD 123319, and CGP 42112 were ineffective. This is illustrated in FIG. 6.

These studies suggest that the inhibition of neurite outgrowth by both peptides is mediated by the AT$_4$ receptors, and supports a role for angiotensin IV in neurite modelling.

EXAMPLE 5

Effect of Angiotensin IV on Spinal Cord Damage

Figure 7:

Glial fibrillary acid protein (GFAP)-positive astrocytes are involved with modelling neurite formation after damage to the spinal cord (Bovolenta et al, 1992). Injury-evoked plasticity is a similar situation to that observed in the developing embryo (Schwartz, 1992). In light of our findings on the ability of spinal cord tissue to bind Ang IV (Example 2), we tested the effect of spinal cord injury on Ang IV binding. Surprisingly, we found a marked elevation of [$^{125}$I]Ang IV binding in damaged spinal cord sections. This is illustrated in FIG. 7.

These results suggest that the AT$_4$ receptor may be a suitable target for alleviation of the effects of spinal cord injury.

EXAMPLE 6

Purification of an Endogenous Brain Peptide which Binds to the AT$_4$ Receptor

The level of Ang IV in the brain is very low to undetectable (DJ Campbell, personal communication). The widespread and characteristic distribution of AT$_4$ receptors in the central nervous system suggests that there may be an as yet unidentified peptide ligand for this receptor. We therefore undertook a search for such a ligand, using conventional protein chemistry purification techniques together with an AT$_4$ receptor assay system in order to detect and monitor substance(s) in extracts of sheep brain which compete for [$^{125}$I]Ang IV binding in this system.

a) $^{125}$AT$_4$ Receptor Binding Assay

The binding of $^{125}$I-Ang IV to bovine adrenal membranes was used as an assay system to screen for AT$_4$ receptor binding activity in sheep cerebral cortex fractions. Bovine adrenal glands obtained from the abbatoir were diced into 1 mm×1 mm blocks, homogenized in 3 ml of a hypotonic buffer (50 mM Tris, 5 mM EDTA, pH 7.4) and then centrifuged for 10 min at 500 g. The supernatant was removed and centrifuged for 20 min at 40,000 g, and the resulting pellet was rehomogenized in 2 ml of hypotonic buffer. Binding assay samples contained bovine adrenal (56 mg of protein as determined by the Biorad protein assay), 0.14 μCi of [$^{125}$I]Ang IV (approximately 260 pM), and 10 μl of test sample, in a total volume of 270 μl in 50 mM Tris buffer, pH 7.4, containing 150 mM sodium chloride, 5 mM EDTA, 100 μM phenylmethylsulfonyl fluoride, 20 μM bestatin, and 0.1% (w/v) bovine serum albumin. The relative potency of the fractions in competing for $^{125}$I-Ang IV binding was determined from a standard curve in which known amounts of unlabelled Ang IV were added ($10^{-10}$ to $10^{-6}$ M). Fractions from each purification step were assayed for their ability to compete for [$^{125}$I]Ang IV binding, with those exhibiting the highest activity undergoing the next purification step.

b) Purification Procedure

Sheep cerebral cortex was homogenized in 2 M acetic acid, (2 ml/g tissue), centrifuged, and the supernatant decanted. A preliminary purification of the extract was performed using a column of preparative C18 material (55–105 mm, Waters). The C18 eluent was lyophilized, reconstituted, and subjected to a series of chromatographic steps, in which fractions were assayed for Ang IV displacement activity. In brief, the chromatographic steps were: three successive reversed-phase HPLC steps, using columns of varying pore size (Deltapak C18, 300°A, and Novapak C18) as well as changing ion-pairing agents, solvents and gradient elution conditions; this was followed by anion exchange, then cation exchange, with final purification on a microbore LC C8 column. The purified active peptide was sequenced using an Applied Biosystems Model 470 A Protein Sequencer with an on-line Model 120A PTH Analyzer.

The sheep cerebral cortex yielded 1.9 nmoles of $AT_4$ receptor binding activity per gram of wet weight after the first C18 Deltapak column. Following the third Poly LC column (55° C.), Ang IV activity coeluted with the major UV absorption peak, and the following peptide sequence was obtained from this peak: Leu-Val-Val-Tyr-Pro-Trp-Thr-Gln-Arg-Phe (SEQ ID NO:1).

A search of protein database records revealed that this sequence corresponded to the amino acid sequence 32–41 of the humane β, δ, γ and ε globin chains and is known as LVV-haemorphin-7.

LVV-haemorphin-7 is a 10 amino acid peptide found in the brain, pituitary, hypothalamus and bone marrow which binds with high affinity to the angiotensin $AT_4$ receptor. The sheep peptide sequence is identical to amino acids 30–39 of the sheep $β_A$, $β_B$, $β_C$, and ε globin precursors (Garner and Lingrel, 1989; Saban and King, 1994), and this sequence is conserved in many species, including human (see for example Karelin et al, 1994). In humans, there are 6 β-globin-like genes ε, $γ^A$, $γ^C$, δ, β and a pseudogene Ψβ, clustered on chromosome 11, and all encode the LVV-haemorphin-7 sequence (Karlsson and Nienhuis, 1985). This sequence is not present in any of the α globin family of genes. LVV-haemorphin-7 and some shorter sequences within this peptide have opioid activity, and it appears that the sequence VVYP is required for this activity (Karellin et al, 1994).

EXAMPLE 7

Properties of Synthetic LVV-haemorphin-7

A decapeptide with the sequence isolated above was synthesized under contract by Chiron Mimotopes, and its biochemical and pharmacological properties were characterized as follows:

a) HPLC

A preliminary high performance liquid chromatography (HPLC) run indicated that the synthetic peptide did not coelute with the fraction that was sequenced. It appeared that the fraction might have been degraded due to prolonged storage at 4° C. Mass spectrometry analysis was carried out in order to determine whether this was the case. The data obtained from mass spectrometry analysis of the two active peaks produced following prolonged storage of the original purified material were indeed consistent with degradation. The early eluting peak gave a mass corresponding exactly to the loss of the phenylalanine residue from the carboxy terminus, whereas the second active peak gave a mass corresponding exactly to the loss of the amino terminal leucine residue. Furthermore, these data (given that all the mass readings were unambiguous) strongly suggest that the active peptide is not post-translationally modified, either in the peptide core or at the amino or carboxyl terminus.

b) Ligand Binding Studies

The pharmacological properties of the decapeptide LVV-haemorphin-7 in competing for the binding of $[^{125}I]$-Ang IV in bovine adrenal membrane and sheep cerebellar cortical membranes were determined. Both LVV-haemorphin-7 and Ang IV were radioiodinated using chloramine T, and separated on a C18 Sep-pak column using 0.5% trifluoroacetic acid in a 20–80% methanol gradient.

Bovine adrenal membranes or sheep cerebellar cortical membranes were homogenized in 30 ml of a hypotonic buffer (50 mM Tris, 5 mM EDTA, pH 7.4), and then centrifuged for 10 min at 500 g. The supernatant was removed and centrifuged for 20 min at 40,000 g, and the resulting pellet was rehomogenized in 2 ml of hypotonic buffer. Binding assays contained:

bovine adrenal (56 μg of protein) or sheep cerebellar membranes (26 μg of protein), as determined by the Biorad protein assay (Bradford, 1976);

0.14 μCi of $[^{125}I]$Ang IV (approximately 260 pM), or 0.11 μCi of $[^{125}I]$LVV-haemorphin-7 (approximately 200 pM), and competing ligand, in a total volume of 270 μl in 50 mM Tris buffer, pH 7.4, containing 150 mM sodium chloride, 5 mM EDTA, 100 μM phenylmethylsulfonyl fluoride, 20 μM bestatin and 0.1% (w/v) bovine serum albumin.

The assay was incubated at 37° C. for 2 h.

In the bovine adrenal membranes, a range of concentrations of unlabelled LVV-haemorphin-7 or Ang IV was added to the assay system in order to determine the relative potencies of the two peptides in this radioreceptor assay system. Both Ang IV and LW-haemorphin-7 displayed comparable affinities in competing for the $^{125}$I-Ang IV binding (approx. 1–5 nM), with Ang IV exhibiting slightly higher affinity.

For competition studies in sheep cerebellar cortical membranes, dilutions of the unlabelled ligands, LVV-haemorphin-7, Ang IV, Ang II, Ang III and the non-specific opioid antagonist, naloxone, the Ang II $AT_1$ antagonist, losartan, the Ang II $AT_2$ antagonist, PD 123319, and the sigma opioid and dopamine $D_2$ antagonist, haloperidol, were used at concentrations ranging from $10^{-13}$ to $10^{-4}$ M. Quantitation of receptor binding was calculated as the mean of two experiments.

Figure 8:
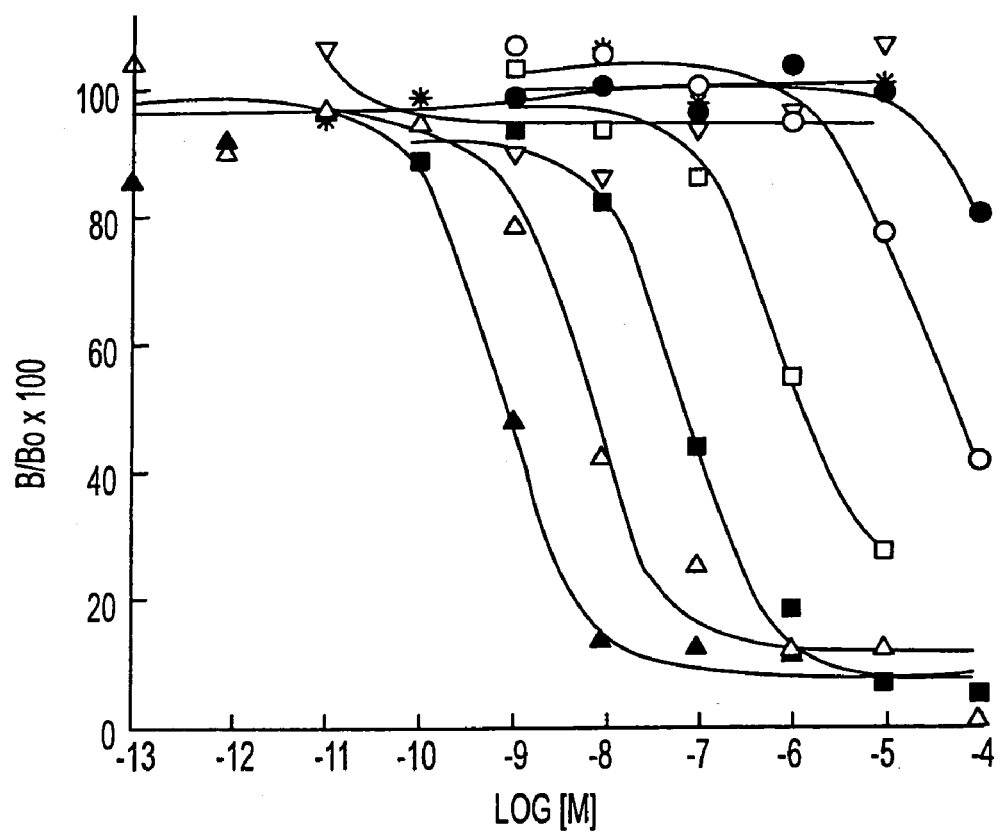
Figure 9:
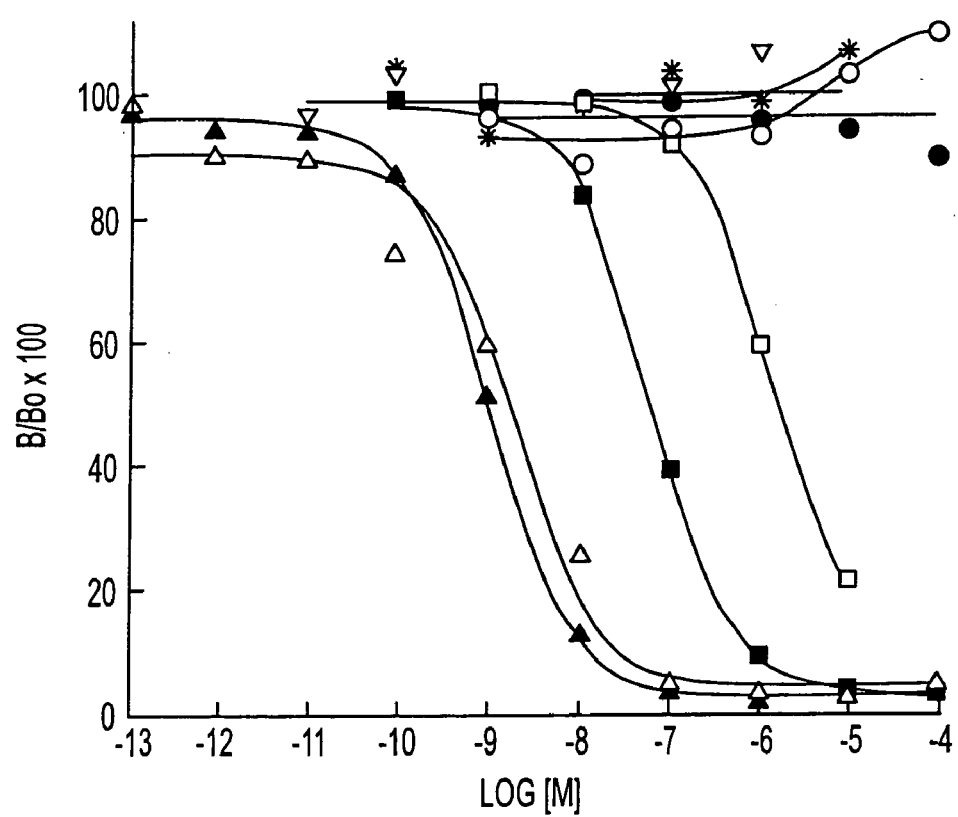

In these studies, $^{125}$I-LVV-haemorphin-7 binding to sheep cerebellar cortical membranes was competed for by LVV-haemorphin-7, Ang IV, Ang III, and Ang II ($IC_{50}$s of 5.6 nM, 1 nM, 77 nM, and 1.6 μM respectively). PD 123319 was a weak competitor ($IC_{50}$ of 46 μM), whilst losartan, naloxone and haloperidol were ineffective ($IC_{50}$ greater than 100 mM). These results are illustrated in FIG. 8. Similarly, $[^{125}I]$Ang IV binding to cerebellar membranes was competed for by Ang IV, LVV-haemorphin-7, Ang III, and Ang II with $IC_{50}$s of 1.13 nM, 2 nM, 6.9 nM and 2 μM respectively, whilst PD 123319, losartan, naloxone and haloperidol were inactive at 10 μM. These results are illustrated in FIG. 9.

c) Binding of $^{125}$1I-LVV-haemorphin-7 to Sheep Brain

Sheep hindbrain sections were used to compare the distribution of $^{125}$I-LVV-haemorphin-7 binding and $AT_4$ receptor sites. Sections at 10 μm thickness were equilibrated to 22° C. (30 min), and then preincubated for 30 min in an isotonic buffer containing 50 mM Tris, 150 mM sodium chloride, 5 mM EDTA, 100 μM phenylmethylsulfonyl fluoride, 20 μM bestatin and 0.1% bovine serum albumin, pH 7.4, before a further 2 h incubation in the same buffer containing 2.84 μCi of $[^{125}I]$LVV-haemorphin-7 or [125I] Ang IV (approximately 140 pM). The binding of the radioligands was cross-displaced with either 1 μM unlabelled LVV-haemorphin-7 or Ang IV. After incubation, the sections were given three 2 min washes in buffer at 4° C., and exposed to X-ray film for 14 to 28 d.

$[^{125}I]$LVV-haemorphin-7 and $[^{125}I]$Ang IV exhibited an identical binding pattern in the sheep hindbrain. Binding was localized to the motor-associated areas, the granular layer of the cerebellum, the inferior olive, hypoglossal and lateral reticular nuclei, to the autonomic regions, the dorsal motor nucleus of the vagus and the nucleus ambiguus, and to the sensory regions, the external cuneate and spinal trigeminal nuclei. The binding of both radioligands was displaced by a 1 µM concentration of either unlabelled Ang IV or LVV-haemorphin-7, indicating that not only are the two binding sites distributed in the same brain regions, but that the two radioligands are actually binding to the same sites.

EXAMPLE 8

Isolation of Potential LVV-Haemorphin-7 Precursor Clones

It is not known whether LVV-haemorphin-7 is synthesized in the brain, or whether it is derived from the breakdown of haemoglobin. Demonstration of LVV-haemorphin-7 precursor mRNA in the brain would provide evidence for the former. Possible methods to demonstrate that LVV-haemorphin-7 precursor mRNA is present in the brain include:

(a) isolation of specific cDNA clones from a brain cDNA library;
(b) detection of the mRNA in the brain by RT-PCR;
(c) detection of LVV-haemorphin-7 precursor MRNA by in situ hybridization histochemistry; and
(d) demonstration of the MRNA in brain specific cell cultures.

It has previously been reported that α- and β-globin mRNAs are expressed in mouse brain, as demonstrated by Northern analysis (ohyagi,Y., et al, 1994).

Each of these approaches has specific advantages. In situ hybridization histochemistry and detection of the mRNA in brain specific cell cultures would provide evidence for synthesis in the brain. Isolation of clones and the reverse transcription polymerase chain reaction (RT-PCR) detection of mRNA would show the presence of mRNA in the brain, but contamination by reticulocytes cannot be excluded. However, isolation of cDNA clones provides considerable information about the structure of the precursor. The precursor of LVV-haemorphin-7 may be a member of the β-globin family, eg $β^A$ etc, or an alternatively spliced globin, or it may be a previously unknown non-globin peptide.

To isolate potential clones that code for the precursor of the LVV-haemorphin-7 peptide, we have screened a rat brain cDNA library using an oligonucleotide based on the LVV-haemorphin-7 sequence.

Oligonucleotide Design

Figures 10A, 10B:
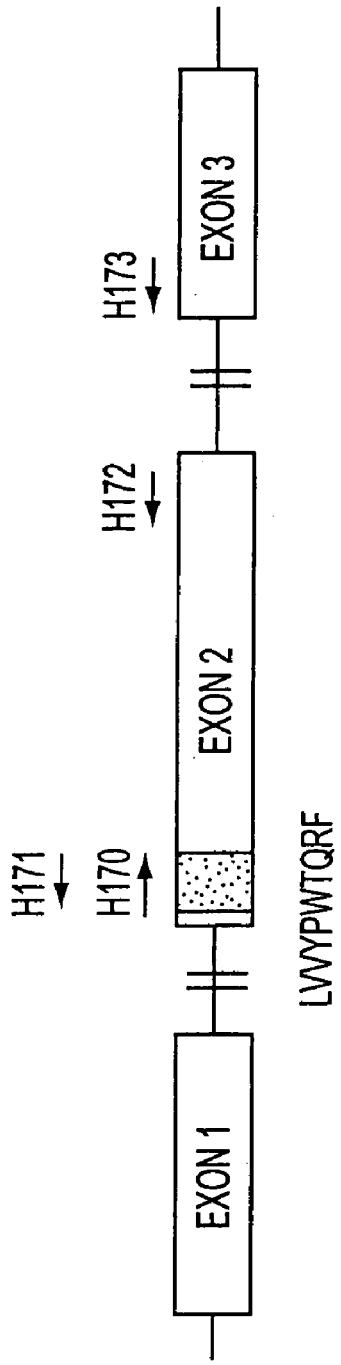

A number of oligonucleotides have been designed, as illustrated in FIG. 10. Oligonucleotide H170 (SEQ ID NO:2) was designed to correspond to the region of the sheep β-globin gene encoding the LVV-haemorphin-7 sequence. This probe was used for screening the library, and also as the sense oligonucleotide in PCR. Oligonucleotide H173 (SEQ ID NO:5) was designed as the antisense primer for use in PCR. PCR with H170/H173 spans intron 2, and will generate a 255 bp fragment with cDNA as the template and a 1098 bp fragment with genomic DNA. Oligonucleotide H172 (SEQ ID NO:4) can be used as an internal probe for H170/H173 PCR products. Oligonucleotide H172 and H173 (SEQ ID NO:4, 5) are antisense probe corresponding to exon 2 and 3 of the sheep β-globin gene, and were used for in situ hybridization histochemistry.

Detection of β-Globin Like Sequences in Brain by Polymerase Chain Reaction (PCR)

RNA was isolated from sheep cerebellar and cerebral cortices, heart and liver. The RNA (20 µg) was reverse transcribed in a 25 µl reaction containing 100 mM KCl, 50 mM Tris-HCl (pH 8.4), 6 mM MgCl$_2$, 10 mM dithiothreitol, 500 µM dNTPs (Progen), 12µg/ml random hexamers (Boehringer Mannheim), 40 units RNasin (Progen), and AMV reverse transcriptase (Boehringer Mannheim, 25 units) at 42° C. for 1 h. An aliquot of the reverse transcription reaction (10%) was used in the polymerase chain reaction. The primers used for amplification of the β-globin mRNA were sense H170 and antisense H173 (see FIG. 10). PCR was performed in a reaction containing: 10 mM Tris-HCl (pH 8.3), 50 mM KCl, 400 µM dNTPs, Taq Polymerase (Bresatec, 2.5 units), 3 µM MgCl$_2$, and each primer at 400 nM. Denaturation, annealing and extension were carried out at 94° C., 60° C. and 72° C. for 1 min each for 40 cycles, followed by a final extension at 72° C. for 10 min.

Figure 11:
FIG. 11 illustrates the detection of β-globin mRNA by RT-PCR and Southern blotting in sheep cerebellar and cerebral cortices, heart and liver. Molecular weight markers are shown on the left.

The PCR products were separated on an agarose gel, transferred to Hybond N+, and Southern analysis using an internal oligonucleotide (H172) was performed to confirm that the products were derived from globin precursors. Specific bands of the expected size of 255 bp were detected in all four tissues examined, as shown in FIG. 11.

Screening a Rat cDNA Library for β-Globin Like Sequences

An oligonucleotide corresponding to the nucleotide sequence of the LVV-haemorphin-7 region of the sheep β-globin (H170) was used to screen a rat brain cDNA library (Stratagene Cat No: 936515, Sprague-Dawley, whole brain). Approximately 8×10$^5$ clones were plated, and plaque lifts taken using standard methods (eg Maniatis et al: Molecular Cloning). The filters were prehybridzed in Rapid-Hyb (Amersham) for 1 hr at 42° C., then the 5' end labelled H170 was added for 2 hr. The filters were then washed 3 times at 42° C. in 2×SSC/0.1% SDS. The filters were autoradiographed for 4 days using Biomax film and an intensifying screen. A total of 24 putative positives was isolated. The positives were eluted in PSB.

The positives were then further characterized using a PCR based method. PCR was performed using oligonucleotide H170 as the 5' primer and H173 as the 3' primer. A PCR product derived from H170/H173 will span an intron in the sheep β-globin gene, and will generate a 1098 bp fragment.

An aliquot of the eluted λ clone was boiled for 5 min, then chilled on ice. This was used as template DNA in a PCR reaction containing 10 mM Tris-HCl (pH 8.3), 50 mM KCl, 400 µM dNTPs, Taq Polymerase (Bresatec, 2.5 units), 3 µM MgCl$_2$, and each primer at 400 nM. Denaturation, annealing and extension were carried out 94° C., 60° C. and 72° C. for 1 min each for 30 cycles, followed by a final extension at 72° C. for 10 min. PCR products were analysed by electrophoresis on a 1.4% agarose gel.

The H170 positive/PCR negative clones were stored for further characterization. It is considered that they may be either non-globin precursors, alternatively spliced precursors or fragments of globin clones.

Sequencing Rat β-Globin Clones

The 6 positives selected by PCR were plaque purified, and subjected to plasmid excision according to the manufacturers instructions. The insert sizes were determined by separate restriction mapping with the enzymes EcoRI and PvuII. Clones EX, FX, LX, RX and TX contain inserts of approx 500 bp. Clone DX was the longest, and contained an insert of approximately 2500 bp. Southern analysis of the clones using an internal oligonucleotide (H172) confirmed that these clones were derived from globin precursors.

These plasmids were sequenced using the Pharmacia T7 sequencing kit. Sequencing of clones EX, FX and LX, using the universal primer, showed sequence homology to the 3' untranslated region of β-globin. Clones RX and TX when sequenced with the universal primer, and clone DX when sequenced with the reverse primer, showed sequence homology to the 5' end of the β-globin gene, including the initiation codon ATG.

Clone DX was subjected to nested deletion analysis to generate more templates for sequencing. This clone contained the β-globin sequence, and approximately 1.8 kb of sequence which was not homologous to the globin cluster, and may be the result of two inserts in the one clone.

Complete sequencing of clone EX showed that the clone was identical to rat $β^A$-globin (Genbank accession No: X16417), as shown in FIG. 12. FIG. 13 shows the nucleotide sequence and derived amino acid sequence of clone EX, indicating the putative LVV-haemorphin-7 region.

EXAMPLE 9

In Situ Hybridization Histochemistry

The distribution of mRNA encoding LVV-haemorphin-7 and its precursor peptide is being investigated using a range of oligonucleotides for the different regions of the β-globin gene, including the C-terminal of exon 2 (H172 of FIG. 13) and the N-terminal regions of exon 3 (H173). The antisense (initially H172, H173) oligonucleotides were 3' end labelled with a $^{35}$S-dATP using terminal d-transferase and purified on a Nensorb column. Sheep brain sections were then hybridized with $7.5 \times 10^5$ cpm of labelled probe in a 75 µl total volume of 50% formamide, 4×SSC, 1× Denhardt's solution, 2% sarcosyl, 20 mM $Na_2PO4$ buffer (pH 7), 10% dextran sulphate, 50 µg/ml herring sperm DNA and 0.2 mM dithiothreitol. After a 16 h hybridization period, the sections were washed four times in 1×SSC, rinsed in distilled water and dehydrated through increasing ethanol and exposed to Hyperfilm β-max. Preliminary experiments using oligonucleotides H172 and H173 detected β-globin MRNA in the inferior colliculus and nucleus of the spinal trigeminal. Further in situ hybridization histochemical studies involve the use of additional antisense and sense synthetic oligonucleotides from different regions of the β-globin sequence to confirm our finding of β-globin MRNA in brain nuclei. The distribution of β-globin mRNA is then compared to our autoradiographic localization of the $AT_4$ receptors in order further to lucidate roles for this novel peptide system.

EXAMPLE 10

Radioimmunoassay and Immunohistochemical Detection of LVV-haemorphin-7

Two sheep were immunized with the LVV-haemorphin-7 sequence conjugated to diphtheria toxoid and both antisera and affinity purified antisera with adequate titre to set up radioimmunoassays for LVV-haemorphin-7 have been obtained. The radioimmunoassay, which is of conventional type, is used to determine the concentration of LVV-haemorphin-7 in different tissues or in specific regions within a tissue, in order to provide us with further information as to other possible physiological actions of the decapeptide.

The antisera are also used immunohistochemically to determine the tissue distribution of LVV-haemorphin-7, particularly in the brain. Guinea pigs are perfused intracardially with 4% paraformaldehyde in phosphate-buffered saline solution, the tissues dissected out and immersed in a 20% sucrose solution overnight. The tissues are then frozen, 5–10 micron sections cut, and endogenous peroxidase blocked by a 30 min incubation in 0.5% hydrogen peroxidase in methanol prior to an overnight incubation with the primary antibody in phosphate-buffered saline containing 3% normal goat serum. After a few washes in phosphate buffered saline, the sections are incubated with the secondary anti-sheep antibody, and detected using the streptavidin-biotin/horseradish peroxidase complex system (Vectastain). The detection of LVV-haemorphin-7 in neurones provides further support that the decapeptide is synthesized within neurones, and thereby may function as a neuropeptide, since we have already shown that its receptor occurs in neurones. Immunohistochemistry is also performed at the electron microscopic level in order to evaluate the subcellular distribution of the peptide, in particular whether it occurs in intracellular storage granules.

The radioimmunoassay for LVV-haemorphin-7 is also employed to investigate the secretion of the peptide from neural tissue. Slices prepared from brain regions found to be rich in LVV-haemorphin-7 immunoreactivity are incubated in Krebs Ringer Bicarbonate buffer at 37° C., and the effects of depolarization by high $K^+$ medium and various secretagogues are evaluated to test whether the peptide is secreted from neurones. Similar experiments are carried out on cultured neuronal cell lines which are found to contain the peptide. Radioimmunoassays of body fluids including plasma and cerebrospinal fluid are used to determine levels of the peptide in these fluids under normal and pathological conditions.

In addition, the subcellular distribution of the peptide is evaluated by radioimmunassay of subcellular fractions from nervous tissues, including synaptosomes, in order to evaluate if the peptide is stored in subcellular granules, as occurs for other secreted neuropeptides.

EXAMPLE 11

Effect of LVV-haemorphin-7 in Passive Avoidance Conditioning Trials

Angiotensin IV has been shown to improve memory retention and retrieval in a passive avoidance task (Braszko et al, 1988, Wright et al, 1993), an effect which was mediated via the $AT_4$ receptor. Scopolamine, a muscarinic receptor antagonist, has been used to induce amnesia. It has been reported that a more stable analogue of angiotensin IV, WSU 2088, reversed the disruption in learning in a passive avoidance task induced by scopolamine. The effects of LVV-haemorphin-7 on the conditioned passive avoidance task in untreated and scopolamine-treated rats were tested.

Rats were surgically implanted with intracerebroventricular cannulae and handled daily. On the conditioning day, each animal was habituated to the dark compartment of a passive avoidance conditioning apparatus for 5 min with the guillotine door closed. The animal was then returned to its home cage for 5 min and then placed in the light compartment with the guillotine door opened. Latency to enter the dark compartment with all four feet was measured in seconds. These trials were repeated with 5 min in the home cage between trials until the rat entered the dark side within 20 seconds. Before the final trial on conditioning day, the rats were randomly divided into four groups: (a) saline followed by saline (b) saline followed by 1.0 nmol LVV-haemorphin-7 in (c) 70 nmol scopolamine followed by saline (d) 70 nmol scopolamine followed by 1.0 nmol LVV-haemorphin-7, all administered in a volume of 2.5 µl intracerebroventricularly 30 min and 5 min before the final trial respectively. On the last trial, the guillotine door was closed and the animals received one low-level shock (0.2 mA) for 1.5 seconds via the grid floor. The animals were then returned to their home cages for 24 hours before being tested once daily for the next four days and the latency periods to reenter the dark compartment were measured. Results are shown in FIG. 14.

In this passive avoidance paradigm, the control animals which received successful conditioning displayed high latencies in entering the darkened compartment, whereas rats treated with scopolamine displayed learning and memory deficits, as indicated by much lower latencies in entering the dark compartment. The mean latencies to enter the dark compartment of rats which received LVV-haemorphin-7 after scopolamine were not significantly different from those of the control rats, indicating that in these rats LVV-haemorphin-7 completely reversed the scopolamine-induced amnesia. However, the rats which received LVV-haemorphin-7 alone performed worse than the scopolamine-treated rats.

These results indicate that LVV-haemorphin-7 successfully counteracts the memory disruption induced by scopolamine treatment. However, administration of the peptide alone was detrimental to learning, which may be due to overstimulation of the neuronal system because of the high dose used.

Effective doses of LVV-haemorphin-7 are determined by conducting dose-response studies with LVV-haemorphin-7 and observing the effects on learning a passive avoidance task in the animals, including those with scopolamine-induced amnesia. Similar studies are also used to determine if the memory disruption caused by LVV-haemorphin-7 is due to excessively high doses of the peptide.

EXAMPLE 12

Effect of LVV-haemorphin-7 in the Water Maze Acquisition Trials

The circular water maze (Morris water maze) consists of a circular tank containing water which has been rendered opaque, with a hidden platform underneath the surface of the water. Scopolamine blocks the trial-to-trial decrease in latency of this task, and this effect appears to be due to impairment of short-term memory. The effect of LVV-haemorphin-7 on the scopolamine-induced amnesia in this task was investigated.

Rats were surgically implanted with intracerebroventricular cannulae and handled daily. On the day of the trial, the rats were introduced into the water maze from different starting positions equidistant from the escape platform. The time taken for each rat to reach the platform was noted. There were four consecutive trials for each animal on each day, with a 60 second rest period between trials. The mean latency period before the animal reached the platform was plotted, and is shown in FIG. 15. On days 1 and 2 of the trial (non-spatial), none of the animals received any drug treatment. Although the scopolamine group displayed increased latency on day 1, the latency on day 2 decreased to control level. The rats were then randomly divided into 3 groups:

(a) the saline control,
(b) 70 nmol scopolamine in 2.5 µl, and
(c) 70 nmol scopolamine followed by 1.0 nmol LVV-haemorphin-7, and were subjected to 5 days of testing. Upon intracerebroventricular treatment with scopolamine 30 min prior to testing, the rats displayed significantly increased latencies in finding the platform, demonstrating deficits in learning. In rats treated with LVV-haemorphin-7 25 min after scopolamine, the scopolamine-induced latency in finding the platform was totally reversed, and these rats were indistinguishable from the control group. Withdrawal of treatment on day 8 brought the latency of scopolamine-treated group back to control levels, indicating that the scopolamine-induced amnesia is reversible.

EXAMPLE 13

Effect of LVV-Haemorphin-7 on Acetylcholine Release in Rat Hippocampus

Acetylcholine is thought to be the major transmitter involved in the processing of cognitive function, since anti-cholinergic drugs induce memory deficit and confusion. In Alzheimer's disease, neuronal loss has been reported in cholinergic-rich areas, particularly in the septohippocampal pathway. Angiotensin $AT_4$ receptors were found in high abundance in the basal nucleus of Meynert, in the CA2 and dentate gyrus of the hippocampus, and in somatic and autonomic preganglionic motoneurones of the monkey brain. This pattern of receptor distribution closely resembles that of cholinergic neurones, and suggests that the $AT_4$ receptors may be associated with cholinergic pathways centrally. Moreover, as shown in Example 12 LVV-haemorphin-7 can reverse the learning deficit induced by scopolamine (a muscarinic receptor antagonist). We therefore postulate that LVV-haemorphin-7 can modulate acetylcholine release from the septohippocampal neurones via the $AT_4$ receptors.

Rats are anaesthetized with sodium pentobarbitone, and stereotaxically implanted with intracerebral guide cannulae either in the dorsal hippocampus (coordinates 3.8 mm caudal to bregma, 2.5 mm lateral to midline, and 3.0 mm ventral to the surface of the skull) or ventral hippocampus (coordinates 5.3 mm caudal to bregma, 5.4 mm lateral to midline, and 6.5 mm ventral to surface of the skull). The guide cannulae are secured with dental cement anchored to three screws in the skull. Dummy probes are then inserted into the guide cannulae to prevent blockade of the cannulae. The rats are allowed to recover for 5–7 days. On the day of the experiment, a microdialysis probe, with a 3 mm dialysis membrane, is inserted through the guide cannula and perfused with artificial cerebrospinal fluid (148 mM NaCl, 3 mM KCl, 1.4 mM CaCl, 0.8 mM MgCl, 1.3 mM $NaH_2PO_4$, 0.2 mM $Na_2HPO_4$, pH 7.4) at a flow rate of 2.0 µl/min. Neostigmine (1.0 µM) is added to the artificial cerebrospinal fluid to facilitate recovery of acetylcholine. Four 20-min baseline samples are collected 1 h after probe insertion, followed by four 20-min samples during the experimental period when LVV-haemorphin-7 (1 µmol dissoolved in artificial cerebrospinal fluid and 1 µM neostigmine) is perfused through the probe. During the recovery period, the peptide perfusion is withdrawn and four 20-min samples are collected.

Acetylcholine in the dialysates is measured by HPLC with electrochemical detection. Acetylcholine and choline are separated on a 10 cm polymer-based analytical column, and then converted to hydrogen peroxide and betaine by an immobilized enzyme reactor (acetylcholinesterase and choline oxidase) coupled to the analytical column. The mobile phase consists of 35 mM sodium phosphate at pH 8.5 supplemented with the antibacterial reagent Kathoon CG.

EXAMPLE 14

Detection of β-Globin Sequences in Different Neuronal Cell Lines by RT-PCR

Total RNA is isolated from the following cell lines:
(a) NG 108 rat glioma-neuroblastoma hybrid,
(b) SKNMC human neuroblastoma, and
(c) PC 12W rat pheochromocytoma. The total RNA is prepared as follows: $10^7$ cells are homogenized in 4 ml of 4M guanidine thiocyanate, 25 mM sodium citrate and 0.05% sodium dodecyl sulphate followed by sequential addition of 0.4 ml of 2 M sodium acetate pH 4.0, 4 ml water saturated phenol, and 0.8 ml of chloroform-isoamyl alcohol. The homogenate is mixed and cooled on ice for 15 min followed by centrifugation at 2000 g for 15 min. The aqueous phase is removed and subjected to 2 phenol-chloroform extractions before RNA is precipitated by the addition of isopropanol.

The mRNAs are then subjected to RT-PCR. cDNA is synthesized from approximately 20 µg of total RNA, using reverse transcriptase and random hexamers. Ten percent of the cDNA product was amplified by PCR through 40 cycles, with each cycle consisting of denaturation at 94° C. for 1 min, annealing of primers at 60° C. for 1 min and primer extension at 72° C. for 1 min, followed by a final 10 min incubation ac 72° C. The primers used were 5'CTGGTTGTCTACCCCTGGACTCAGAG3' (SEQ ID NO:2), and 5'CAGCACAACCACTAGCACATTGCC3' (SEQ ID NO:5), which corresponded with high homology to sheep β, δ, ε globin chains and flanked a 255 bp cDNA fragment. The sense primer spans the nucleotide sequence which coded for LVV-haemorphin-7, and the antisense primer spans the second intron of the globin gene, to enable cDNA to be distinguished from contaminating genomic DNA. The PCR products are transferred to a Hybond N+ membrane by downward Southern blotting in 0.4 M NaOH. The membrane is hybridized at 42° C. in 5×SSC, 5× Denhardt's solution and 0.5% sodium dodecyl sulphate, with a $^{32}$p end-labelled oligonucleotide 5'CTCAGGATCCACATGCAGCTTATCACAG3' (SEQ ID NO:3), which is internal to the primers used for PCR and binds to β, δ and ε globin chains. After 12 h of hybridization, the filter is washed at 42° C. in a buffer with a final stringency of 0.5×SSC and 0.1% sodium dodecyl sulphate.

We have mapped the distribution of $AT_4$ receptors in the brain of *Macaca fascicularis* and sheep spinal cord. The receptor has a striking and unique distribution, including motor- and sensory-associated regions and pathways and cholinergic cell bodies, including all motor nuclei in the brain stem and spinal cord. We have demonstrated that Ang IV inhibits neurite outgrowth in cultured embryonic chicken neurones, and that this peptide may therefore have a role in growth and development of the central and peripheral nervous systems.

We have purified an endogenous brain peptide which binds to the $AT_4$ receptor with high affinity. This decapeptide is 100% identical to the internal amino-acid sequence 30–39 of sheep β-globin. The presence of this β-globin-like sequence was demonstrated in sheep brain and other tissues using PCR. Screening of a rat brain cDNA library led to the isolation of a clone identical in sequence to rat $β^4$-globin.

We have demonstrated the presence of β-globin mRNA in brain tissue and isolated a β-globin cDNA clone from a rat brain library. These data suggest that LVV-haemorphin-7 is derived from β-globin precursors synthesized in the brain, although contamination by reticulocytes cannot be excluded. All of the cDNA clones sequenced correspond to the sequence encoding rat $β^4$-globin. The rat LVV-haemorphin-7 peptide sequence has a conservative substitution at position 10, with a tyrosine replacing a phenylalanine.

It therefore appears that a peptide corresponding to the sequence of the bovine LVV-haemorphin-7 exists in brain, and is derived from β-globin as precursor. The peptide is almost certainly an endogenous ligand for abundant brain $AT_4$ receptors, and may therefore exert a range of actions on defined motor sensory and cholinergic neurones.

We have shown that LVV-haemorphin-7 reverses the memory-disruptive effects of scopolamine in both passive avoidance conditioning trials and in water maze acquisition trials. However, administration of high doses of the peptide may be detrimental to learning due to overstimulation of the neuronal system.

In a wider context, our findings suggest that β-globin may be a precursor of a range of neuroactive peptides generated in the central nervous system by specific cleavage enzymes to interact with a range of receptors.

It will be apparent to the person skilled in the art that while the invention has been described in some detail for the purposes of clarity and understanding, various modifications and alterations to the embodiments and methods described herein may be made without departing from the scope of the inventive concept disclosed in this invention.

References cited herein are listed on the following pages, and are incorporated by this reference.

REFERENCES

1. Bovolenta, P., Wandosell, F., Nieto-Sampedro, M., *Prog. Brain Res.*, 1992 94 367–379
2. Braszko, J. J., Kupryszewski, G., Witczuk, B. and Wisniewski, K. *Neurosci.*, 1988 27 777–783.
3. Garner, K. J. and Lingrel, J. B. *J. Mol. Evol.*, 1989 28 (3) 175–184
4. Haberl, R. L., Decker, P. J. and Einhaupl, K. M., *Circ. Res.*, 1991 68 1621–1627.
5. Karksson, S. and Nienhuis, A. W. Ann. Rev. Biochem., 1985 54 1071–1108
6. Karelin, A. A., Philippova, M. M., Karelina, E. V. and Ivanov, V. T. Biochem. Biophys. Res. Comm., 1994 202 410–415
7. Miller-Wing, A. V., Hanesworth, J. M., Sardinia, M. F., Hall, K. L., Wright, J. W., Speth, R. C., Grove, K. L. and Harding, J. W. *J. Pharmacol. Exp. Ther.* 266 (1993) 1718–1726.
8. Moeller, I., Chai, S. Y., Oldfield, B. J., McKinley, M. J., Casley, D. and Mendelsohn, F. A. O. *Brain Res.*, 1995 701 301–306.
9. Moeller, J., Paxinos, G, Mendelsohn, F. A. O., Aldred, G. P., Casley, D and Chai, S. y., *Brain Ros*, 1996 712 307–324.
10. Ohyagi, Y., Yamada, T. and Goto, I. Brain Res., 1994 635 323–327
11. Roberts, K. A., Krebs, L. T., Kramar, E. A., Shaffer, M. J., Harding, J. W. and Wright, J. W. *Brain Res.*, 1995 682 13–21.

12. Saban, J. and King, D. Biochim. Biophys. Acta., 1994 1218 87–90
13. Sardinia, M. F., Hanesworth, J. M., Krebs, L. T. and Harding, J. W. *Peptides.* 14 (1993) 949–954.
14. Swanson, G. N., Hanesworth, J. M., Sardinia, M. F., Coleman, J. K. M., Wright, J. W., Hall, K. L., Miller-Wing, A. V., Stobb, J. W., Cook, V. I., Harding, E. C. and Harding, J. W. *Reg. Peptides,* 1992 40 409–419.
15. Schwartz, J. P. *Int. Rev. Neurobiol.* 34 (1992) 1–23.
16. Wong, P. C., Hart, S. D., Zaspel, A. M., Chiu, A. T., Ardecky, R. J., Smith, R. D. and Timmermans, P. B. *J. Pharmacol. Exp. Ther.* 255 (1990) 584–592.
17. Wright, J. W., Miller-Wing, A. V., Shaffer, M. J., Higginson, C., Wright, D. E., Hanesworth, J. M. and Harding, J. W. *Brain Res. Bull.,* 1993 32 497–502.
18. Wright, J. W., Krebs, L. T., Stubb, J. W. and Harding, J. W. Neuroendocrinology, 1995 16 23–52

What is claimed is:

1. A method of modulating a biological activity comprising administering a neuroactive peptide comprising Leu-Val-Val-Tyr-Pro-Trp-Thr-Gln-Arg-Phe, (SEQ ID NO:1)

to a mammal in an amount effective to facilitate said biological activity, wherein said biological activity is selected from the group consisting of learning and short-term memory retrieval.

2. The method of claim 1, wherein the mammal is human.

3. The method of claim 1, wherein the peptide is administered as a composition further comprising a pharmaceutically acceptable carrier.

4. The method of claim 1, wherein said peptide is administered in an amount effective for treating an abnormality in said biological activity.

5. The method of claim 1, wherein the peptide is administered intracerebrally.

6. The method of claim 4, wherein the peptide is administered intracerebrally.

7. A method according to claim 1, wherein said neuroactive peptide additionally has vasoactive effects, dilates cerebral arteries, or increases renal blood flow.

8. A method according to claim 1, wherein said neuroactive peptide comprises one or more D-amino acids.

9. A method according to claim 4, wherein said neuroactive peptide comprises one or more D-amino acids.

* * * * *

SEQUENCE LISTING

```
<160> NUMBER OF SEQ ID NOS: 10

<210> SEQ ID NO 1
<211> LENGTH: 10
<212> TYPE: PRT
<213> ORGANISM: Unknown Organism
<220> FEATURE:
<223> OTHER INFORMATION: Description of Unknown Organism: Beta globin
      precursor

<400> SEQUENCE: 1

Leu Val Val Tyr Pro Trp Thr Gln Arg Phe
 1               5                  10

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 2
ctggttgtct acccctggac tcagag                                         26

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 3
ctctgagtcc agggtagac aaccag                                          26

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 4
ctcaggatcc acatgcagct tatcacag                                       28

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 5
cagcacaacc actagcacat tgcc                                           24
```

```
<210> SEQ ID NO 6
<211> LENGTH: 613
<212> TYPE: DNA
<213> ORGANISM: Rattus sp.

<400> SEQUENCE: 6
cacaaactca gaaacagaca ccatggtgca cctgactgat gctgagaagg ctgctgttaa      60
tggcctgtgg ggaaaggtga accctgatga tgttggtggc gaggccctgg gcaggctgct     120
ggttgtctac ccttggaccc agaggtactt tgatagcttt ggggacctgt cctctgcctc     180
tgctatcatg gtaaccctaa ggtgaaggc ccatggcaag aagtgataa acgccttcaa       240 tgatggcctg aaacacttgg acaacctcaa gggcaccttt gctcatctga gtgaactcca    300
ctgtgacaag ctgcatgtgg atcctgagaa cttcaggctc ctgggcaata tgattgtgat    360
tgtgttgggc caccacctgg gcaaggaatt caccccctgt gcacaggctg ccttccagaa    420
ggtggtggct ggagtggcca gtgccctggc tcacaagtac cactaaacct ctttttcctgc   480 tcttgtcttt gtgcaatggt caattgttcc caagagagca tctgtcagtt gttgtcaaaa    540
tgacaaagac ctttgaaaat ctgtcctact aataaaaggc atttactttc actgcaaaaa    600
aaaaaaaaaa aaa                                                        613

<210> SEQ ID NO 7
<211> LENGTH: 613
<212> TYPE: DNA
<213> ORGANISM: Rattus sp.
<220> FEATURE:
<221> NAME/KEY: CDS
<222> LOCATION: (23)..(463)

<400> SEQUENCE: 7
cacaaactca gaaacagaca cc atg gtg cac ctg act gat gct gag aag gct       52
                         Met Val His Leu Thr Asp Ala Glu Lys Ala
                          1               5                  10 gct gtt aat ggc ctg tgg gga aag gtg aac cct gat gat gtt ggt ggc       100
Ala Val Asn Gly Leu Trp Gly Lys Val Asn Pro Asp Asp Val Gly Gly
             15                  20                  25 gag gcc ctg ggc agg ctg ctg gtt gtc tac cct tgg acc cag agg tac       148
Glu Ala Leu Gly Arg Leu Leu Val Val Tyr Pro Trp Thr Gln Arg Tyr
     30                  35                  40 ttt gat agc ttt ggg gac ctg tcc tct gcc tct gct atc atg ggt aac       196
Phe Asp Ser Phe Gly Asp Leu Ser Ser Ala Ser Ala Ile Met Gly Asn
 45                  50                  55 cct aag gtg aag gcc cat ggc aag aag gtg ata aac gcc ttc aat gat       244
Pro Lys Val Lys Ala His Gly Lys Lys Val Ile Asn Ala Phe Asn Asp
         60                  65                  70 ggc ctg aaa cac ttg gac aac ctc aag ggc acc ttt gct cat ctg agt       292
Gly Leu Lys His Leu Asp Asn Leu Lys Gly Thr Phe Ala His Leu Ser
 75                  80                  85                  90 gaa ctc cac tgt gac aag ctg cat gtg gat cct gag aac ttc agg ctc       340
Glu Leu His Cys Asp Lys Leu His Val Asp Pro Glu Asn Phe Arg Leu
             95                 100                 105 ctg ggc aat atg att gtg att gtg ttg ggc cac cac ctg ggc aag gaa       388
Leu Gly Asn Met Ile Val Ile Val Leu Gly His His Leu Gly Lys Glu
        110                 115                 120 ttc acc ccc tgt gca cag gct gcc ttc cag aag gtg gtg gct gga gtg       436
Phe Thr Pro Cys Ala Gln Ala Ala Phe Gln Lys Val Val Ala Gly Val
    125                 130                 135 gcc agt gcc ctg gct cac aag tac cac taaacctctt ttcctgctct             483
Ala Ser Ala Leu Ala His Lys Tyr His
140                 145
```

-continued

```
tgtctttgtg caatggtcaa ttgttcccaa gagagcatct gtcagttgtt gtcaaaatga      543
caaagacctt tgaaaatctg tcctactaat aaaaggcatt tactttcact gcaaaaaaaa      603
aaaaaaaaaa                                                             613
```

<210> SEQ ID NO 8
<211> LENGTH: 147
<212> TYPE: PRT
<213> ORGANISM: Rattus sp.

<400> SEQUENCE: 8

```
Met Val His Leu Thr Asp Ala Glu Lys Ala Val Asn Gly Leu Trp
 1               5                  10                  15

Gly Lys Val Asn Pro Asp Val Gly Gly Glu Ala Leu Gly Arg Leu
                20                  25                  30

Leu Val Val Tyr Pro Trp Thr Gln Arg Tyr Phe Asp Ser Phe Gly Asp
            35                  40                  45

Leu Ser Ser Ala Ser Ala Ile Met Gly Asn Pro Lys Val Lys Ala His
    50                  55                  60

Gly Lys Lys Val Ile Asn Ala Phe Asn Asp Gly Leu Lys His Leu Asp
65                  70                  75                  80

Asn Leu Lys Gly Thr Phe Ala His Leu Ser Glu Leu His Cys Asp Lys
                85                  90                  95

Leu His Val Asp Pro Glu Asn Phe Arg Leu Leu Gly Asn Met Ile Val
            100                 105                 110

Ile Val Leu Gly His His Leu Gly Lys Glu Phe Thr Pro Cys Ala Gln
        115                 120                 125

Ala Ala Phe Gln Lys Val Val Ala Gly Val Ala Ser Ala Leu Ala His
    130                 135                 140

Lys Tyr His
145
```

<210> SEQ ID NO 9
<211> LENGTH: 620
<212> TYPE: DNA
<213> ORGANISM: Unknown Organism
<220> FEATURE:
<223> OTHER INFORMATION: Description of Unknown Organism: RNBGLO

<400> SEQUENCE: 9

```
tgcttctgac atagttgtgt tgactcacaa actcagaaac agacaccatg gtgcacctga       60
ctgatgctga aaggctgct gttaatggcc tgtggggaaa ggtgaaccct gatgatgttg      120
gtggcgaggc cctgggcagg ctgctggttt tctaccttg gacccagagg tactttgata      180
gctttgggga cctgtcctct gcctctgcta tcatgggtaa ccctaaggtg aaggcccatg      240
gcaagaaggt gataaacgcc ttcaatgatg gcctgaaaca cttggacaac ctcaagggca      300
cctttgctca tctgagtgaa ctccactgtg acaagctgca tgtggatcct gagaacttca      360
ggctcctggg caatatgatt gtgattgtgt tgggccacca cctgggcaag gaattcaccc      420
cctgtgcaca ggctgccttc cagaaggtgg tggctggagt ggccagtgcc ctggctcaca      480
agtaccacta aacctctttt cctgctcttg tctttgtgca atggtcaatt gttcccaaga      540
gagcatctgt cagttgttgt caaaatgaca aagacctttg aaaatctgtc ctactaataa      600
aaggcattta ctttcactgc                                                 620
```

<210> SEQ ID NO 10

-continued

```
<211> LENGTH: 6
<212> TYPE: PRT
<213> ORGANISM: Unknown Organism
<220> FEATURE:
<223> OTHER INFORMATION: Description of Unknown Organism: Hexapeptide

<400> SEQUENCE: 10

Val Tyr Ile His Pro Phe
 1               5
```